(12) United States Patent
Klun et al.

(10) Patent No.: US 9,790,396 B2
(45) Date of Patent: Oct. 17, 2017

(54) ARTICLES INCLUDING A (CO)POLYMER REACTION PRODUCT OF A URETHANE (MULTI)-(METH)ACRYLATE (MULTI)-SILANE

(71) Applicant: 3M INNOVATIVE PROPERTIES COMPANY, St. Paul, MN (US)

(72) Inventors: Thomas P. Klun, Lakeland, MN (US); Alan K. Nachtigal, Minneapolis, MN (US); Joseph C. Spagnola, Woodbury, MN (US); Mark A. Roehrig, Stillwater, MN (US); Jennifer K. Schnobrich, St. Paul, MN (US); Guy D. Joly, Shoreview, MN (US); Christopher S. Lyons, St. Paul, MN (US)

(73) Assignee: 3M INNOVATION PROPERTIES COMPANY, St. Paul, MN (US)

( * ) Notice: Subject to any disclaimer, the term of this patent is extended or adjusted under 35 U.S.C. 154(b) by 318 days.

(21) Appl. No.: 14/416,303

(22) PCT Filed: Mar. 1, 2013

(86) PCT No.: PCT/US2013/028518
§ 371 (c)(1),
(2) Date: Jan. 22, 2015

(87) PCT Pub. No.: WO2014/025387
PCT Pub. Date: Feb. 13, 2014

(65) Prior Publication Data
US 2015/0203708 A1    Jul. 23, 2015

Related U.S. Application Data

(60) Provisional application No. 61/680,995, filed on Aug. 8, 2012, provisional application No. 61/681,003, filed
(Continued)

(51) Int. Cl.
*C09D 143/04* (2006.01)
*C07F 7/18* (2006.01)
(Continued)

(52) U.S. Cl.
CPC ............. *C09D 143/04* (2013.01); *B05D 1/60* (2013.01); *B05D 3/067* (2013.01); *B05D 3/068* (2013.01); *B05D 3/101* (2013.01); *B32B 27/308* (2013.01); *C07F 7/1868* (2013.01); *C08F 130/08* (2013.01); *C08J 7/045* (2013.01); *C08K 3/34* (2013.01); *C09D 133/14* (2013.01); *C09D 135/02* (2013.01); *C09J 133/14* (2013.01); *C23C 14/08* (2013.01); *C23C 14/34* (2013.01); *C23C 16/40* (2013.01); *C23C 16/44* (2013.01); *H01L 51/004* (2013.01); *H01L 51/107* (2013.01); *H01L 51/448* (2013.01); *H01L 51/5253* (2013.01); *B32B 2250/04* (2013.01); *B32B 2307/7242* (2013.01); *B32B 2307/7244* (2013.01); *C08J 2333/12* (2013.01); *Y10T 428/1064* (2015.01); *Y10T 428/31507* (2015.04); *Y10T 428/31551* (2015.04);
(Continued)

(58) Field of Classification Search
CPC .... B32B 2307/7242; B32B 2307/7244; B32B 2307/7246
See application file for complete search history.

(56) References Cited

U.S. PATENT DOCUMENTS

| 3,600,216 A | 8/1971 | Stewart |
| 4,378,250 A | 3/1983 | Treadway |

(Continued)

FOREIGN PATENT DOCUMENTS

| CN | 1154087 A | 7/1997 |
| CN | 1615323 A | 5/2005 |

(Continued)

OTHER PUBLICATIONS

A. Matei; Functionalized ormosil scaffolds processed by direct laser polymerization for application in tissue engineering; Applied Surface Science, Oct. 26, 2012; vol. 278, p. 357-361.
Affinito, "Polymer-Oxide Transparent Barrier Layers", Society of Vacuum Coaters 39th Annual Technical Conference Proceedings, 1996, pp. 392-397.
Affinito, "Vacuum Deposited Polymer/Metal Multilayer Films for Optical Application", Thin Solid Films, 1995, vol. 270, pp. 43-48.
Ling, "Synthesis and Characterization of new monomers and Polymers Containing Hindered Piperidine Groups", Journal of macromolecular Science, Part A: Pure and Applied Chemistry, 1998, vol. A35, No. 7&8, pp. 1327-1336.
(Continued)

*Primary Examiner* — Marc Zimmer
(74) *Attorney, Agent, or Firm* — James A. Baker

(57) ABSTRACT

Urethane (multi)-(meth)acrylate (multi)-silane compositions, and articles including a (co)polymer reaction product of at least one urethane (multi)-(meth)acrylate (multi)-silane precursor compound. The disclosure also articles including a substrate, a base (co)polymer layer on a major surface of the substrate, an oxide layer on the base (co)polymer layer; and a protective (co)polymer layer on the oxide layer, the protective (co)polymer layer including the reaction product of at least one urethane (multi) (meth)acrylate (multi)-silane precursor compound. The substrate may be a (co)polymeric film or an electronic device such as an organic light emitting device, electrophoretic light emitting device, liquid crystal display, thin film transistor, or combination thereof. Methods of making urethane (multi)-(meth)acrylate (multi)-silane precursor compounds and their use in composite multilayer barrier films are also described. Methods of using such barrier films in articles selected from a solid state lighting device, a display device, and combinations thereof, are also described.

20 Claims, 1 Drawing Sheet

Related U.S. Application Data on Aug. 8, 2012, provisional application No. 61/681,008, filed on Aug. 8, 2012, provisional application No. 61/681,023, filed on Aug. 8, 2012, provisional application No. 61/681,051, filed on Aug. 8, 2012.

(51) Int. Cl.

| | | |
|---|---|---|
| H01L 51/00 | (2006.01) | |
| H01L 51/52 | (2006.01) | |
| H01L 51/44 | (2006.01) | |
| H01L 51/10 | (2006.01) | |
| B05D 3/06 | (2006.01) | |
| B32B 27/30 | (2006.01) | |
| C08J 7/04 | (2006.01) | |
| C09D 133/14 | (2006.01) | |
| B05D 1/00 | (2006.01) | |
| B05D 3/10 | (2006.01) | |
| C08K 3/34 | (2006.01) | |
| C09D 135/02 | (2006.01) | |
| C23C 14/08 | (2006.01) | |
| C23C 14/34 | (2006.01) | |
| C23C 16/40 | (2006.01) | |
| C23C 16/44 | (2006.01) | |
| C08F 130/08 | (2006.01) | |
| C09J 133/14 | (2006.01) | |

(52) U.S. Cl.
CPC .................. *Y10T 428/31609* (2015.04); *Y10T 428/31663* (2015.04)

(56) References Cited

U.S. PATENT DOCUMENTS

| | | | |
|---|---|---|---|
| 4,650,889 A | 3/1987 | Plueddemann | |
| 4,696,719 A | 9/1987 | Bischoff | |
| 4,722,515 A | 2/1988 | Ham | |
| 4,842,893 A | 6/1989 | Yializis | |
| 4,889,768 A * | 12/1989 | Yokoshima | C03C 25/106 427/180 |
| 4,954,371 A | 9/1990 | Yializis | |
| 4,983,737 A | 1/1991 | Ravichandran | |
| 5,018,048 A | 5/1991 | Shaw | |
| 5,032,461 A | 7/1991 | Shaw | |
| 5,097,800 A | 3/1992 | Shaw | |
| 5,125,138 A | 6/1992 | Shaw | |
| 5,142,012 A | 8/1992 | Furukawa | |
| 5,233,006 A | 8/1993 | Wolter | |
| 5,384,342 A * | 1/1995 | Szum | C03C 17/32 428/378 |
| 5,399,738 A | 3/1995 | Wolter | |
| 5,440,446 A | 8/1995 | Shaw | |
| 5,442,071 A | 8/1995 | Galbo | |
| 5,532,398 A | 7/1996 | Wolter | |
| 5,547,908 A | 8/1996 | Furuzawa | |
| 5,654,084 A | 8/1997 | Egert | |
| 5,696,179 A | 12/1997 | Chawla | |
| 5,770,301 A | 6/1998 | Murai | |
| 5,866,651 A | 2/1999 | Moren | |
| 5,877,895 A | 3/1999 | Shaw | |
| 5,888,491 A | 3/1999 | Mitra et al. | |
| 5,891,958 A * | 4/1999 | Nambu | C09D 143/04 428/446 |
| 6,010,751 A | 1/2000 | Shaw | |
| 6,045,864 A | 4/2000 | Lyons | |
| 6,214,422 B1 | 4/2001 | Yializis | |
| 6,231,939 B1 | 5/2001 | Shaw | |
| 6,335,479 B1 | 1/2002 | Yamada | |
| 6,358,863 B1 | 3/2002 | Desu | |
| 6,413,645 B1 | 7/2002 | Graff | |
| 6,522,067 B1 | 2/2003 | Graff | |
| 6,531,560 B1 | 3/2003 | Campbell | |
| 6,548,912 B1 | 4/2003 | Graff | |
| 6,573,652 B1 | 6/2003 | Graff | |
| 6,815,043 B2 | 11/2004 | Fleming | |
| 6,835,950 B2 | 12/2004 | Brown | |
| 6,852,393 B2 | 2/2005 | Gandon | |
| 6,866,901 B2 | 3/2005 | Burrows | |
| 7,018,713 B2 | 3/2006 | Padiyath | |
| 7,943,062 B2 | 5/2011 | Swager | |
| 8,129,205 B2 | 3/2012 | Rana | |
| 8,193,698 B2 | 6/2012 | Klein | |
| 8,221,176 B2 | 7/2012 | Yoo | |
| 8,399,102 B2 | 3/2013 | Oertli | |
| 2003/0049995 A1 | 3/2003 | Schutz | |
| 2003/0203210 A1 | 10/2003 | Graff | |
| 2004/0032658 A1 | 2/2004 | Fleming | |
| 2004/0195967 A1 | 10/2004 | Padiyath et al. | |
| 2004/0265602 A1 | 12/2004 | Kobayashi | |
| 2005/0119421 A1 | 6/2005 | Schindler et al. | |
| 2006/0057398 A1 | 3/2006 | Zimmermann | |
| 2007/0020451 A1 | 1/2007 | Padiyath | |
| 2007/0135572 A1 | 6/2007 | Wolter | |
| 2007/0185270 A1 | 8/2007 | Arndt | |
| 2007/0286993 A1 | 12/2007 | Radcliffe | |
| 2008/0196664 A1 | 8/2008 | David | |
| 2009/0208719 A1 | 8/2009 | Kang | |
| 2009/0214879 A1 | 8/2009 | Jucker | |
| 2010/0039028 A1 | 2/2010 | Suzuki | |
| 2010/0119840 A1 | 5/2010 | Padiyath et al. | |
| 2010/0210862 A1 | 8/2010 | Tsuchida et al. | |
| 2011/0081502 A1 | 4/2011 | Bright | |
| 2011/0223434 A1 | 9/2011 | Roehrig | |
| 2012/0003448 A1 | 1/2012 | Weigel | |
| 2012/0003451 A1 | 1/2012 | Weigel | |
| 2012/0003484 A1 | 1/2012 | Roehrig et al. | |
| 2012/0160402 A1 | 6/2012 | Ho | |
| 2012/0164434 A1 | 6/2012 | Ramadas | |
| 2012/0301634 A1 | 11/2012 | Nakamura | |
| 2012/0301635 A1 * | 11/2012 | Hasegawa | C08J 7/042 428/1.32 |
| 2013/0164546 A1 | 6/2013 | Oertli | |
| 2013/0260144 A1 | 10/2013 | Yamazaki | |
| 2015/0203707 A1 | 7/2015 | Klun | |

FOREIGN PATENT DOCUMENTS

| | | |
|---|---|---|
| CN | 1771127 A | 5/2006 |
| EP | 2186866 A | 5/2010 |
| EP | 2529926 A | 12/2012 |
| JP | 1-110572 | 4/1989 |
| JP | H01-304108 A | 12/1989 |
| JP | 2-130139 | 5/1990 |
| JP | H02-133338 A | 5/1990 |
| JP | H08-512256 A | 12/1996 |
| JP | H11-503937 A | 4/1999 |
| JP | 2001-270859 | 10/2001 |
| JP | WO02/102812 | * 12/2002 |
| JP | 2003-238795 | 8/2003 |
| JP | 2004-35591 | 2/2004 |
| JP | 2005-122147 A | 5/2005 |
| JP | 2006-525152 A | 11/2006 |
| JP | 2008-111025 | 5/2008 |
| JP | 2009-246360 | 10/2009 |
| JP | 2009-256575 A | 11/2009 |
| JP | 2010-023234 A | 2/2010 |
| JP | 2010-121013 A | 3/2010 |
| JP | 2010-111846 A | 5/2010 |
| JP | 2010-215902 | 9/2010 |
| JP | 2011-079926 | 4/2011 |
| JP | 2011-079926 A | 4/2011 |
| JP | 2013-035275 A | 2/2013 |
| JP | 2015-530427 A | 10/2015 |
| JP | 2015-532663 A | 12/2015 |
| KR | 2009-0113576 | 11/2009 |
| KR | 2011-0001334 | 1/2011 |
| TW | 200508296 A | 3/2005 |
| TW | 201226193 A1 | 7/2012 |
| WO | WO 00-26973 | 5/2000 |
| WO | WO 01-98393 | 12/2001 |
| WO | WO 02-102812 | 12/2002 |
| WO | WO 2006/109496 A1 | 10/2006 |

(56) References Cited

FOREIGN PATENT DOCUMENTS

| WO | WO 2006/132180 A | | 12/2006 |
|---|---|---|---|
| WO | WO 2008-122292 | | 10/2008 |
| WO | WO 2009-126115 | | 10/2009 |
| WO | WO 2010/0044321 | | 4/2010 |
| WO | WO 2010-056559 | | 12/2010 |
| WO | WO 2011/0086958 | | 7/2011 |
| WO | WO 2011/093286 A1 | | 8/2011 |
| WO | WO2011/129413 | * | 10/2011 |
| WO | WO 2012/003198 A2 | | 1/2012 |
| WO | WO 2012-003416 | | 1/2012 |
| WO | WO 2012074030 A1 | | 6/2012 |
| WO | WO 2012-106184 | | 8/2012 |
| WO | WO 2014-025383 | | 2/2014 |
| WO | WO 2014-025384 | | 2/2014 |
| WO | WO 2014-025385 | | 2/2014 |
| WO | WO 2014-025386 | | 2/2014 |

OTHER PUBLICATIONS

Ling, "Synthesis and Polymerization of New Methacryloyl Ureas Carrying a Hindered Piperidine and a Hydroxyl Group", Journal of Macromolecular Science Part A: Pure and Applied Chemistry, 2001, vol. A38, No. 2, pp. 137-158.

Plueddemann, "New Coupling Agents for improved Corrosion Resistant Composites", Polymer-Plastics Technology and Engineering, Sep./Dec. 1986, pp. 223-231.

Shaw, "A New Vapor Deposition Process for Coating Paper and Polymer Webs", Technical paper Presented at The Sixth International Vacuum Web Coating Conference in Reno, Oct. 28, 1992, pp. 18-24.

Shaw, RadTec' 96 North America UV/EB Conference Proceedings, "Use of Evaporated Acrylate Coatings to Smooth the Surface of Polyester and Polypropylene Film Substrates", 701-707 (1996).

Shaw, "Use of Vapor Deposited Acrylate Coatings to Improve the Barrier Properties of Metallized Film", Society of Vacuum Coaters 37th Annual Technical Conference Proceedings, 1994, pp. 240-247.

Shaw, "A New High Speed Process for Vapor Depositing Acrylate Thin Films: An Update", Society of Vacuum Coaters 36th Annual Technical Conference Proceedings, 1993, pp. 348-351.

Swanson, "Measurement of Web Curl", Applied Web Handling Conference 2006, 2006, 30 pages.

International Search Report for PCT International Application No. PCT/US2013/028518 mailed on Jun. 26, 2013, 4 pages.

Saunders and Frisch, "Polyurethanes: Chemistry and Technology" 1963 (Part I) and 1964 (Part II), Interscience Publishers, New York.

Photopolymerization experiments and properties of some urehtane/urea methacrylates tested in dental composites, retrieved Jul. 25, 2017.

Office Action dated Aug. 11, 2017—U.S. Appl. No. 14/417,831.

* cited by examiner

ARTICLES INCLUDING A (CO)POLYMER REACTION PRODUCT OF A URETHANE (MULTI)-(METH)ACRYLATE (MULTI)-SILANE

CROSS REFERENCE TO RELATED APPLICATIONS

This application claims the benefit of U.S. Provisional Application Nos. 61/681,003; 61/681,008; 61/681,023; 61/681,051; and 61/680,995, all filed on Aug. 8, 2012, the disclosures of which are incorporated by reference herein in their entireties.

FIELD

The present disclosure relates to the preparation of articles including a (co)polymer reaction product of a urethane (multi)-(meth)acrylate (multi)-silane precursor compound. More particularly, the disclosure relates to vapor-deposited protective (co)polymer layers including the reaction product of at least one urethane (multi)-(meth)acrylate (multi)-silane precursor compound, and their use in preparing composite barrier assemblies used in articles and multilayer composite barrier films.

BACKGROUND

Inorganic or hybrid inorganic/organic layers have been used in thin films for electrical, packaging and decorative applications. These layers can provide desired properties such as mechanical strength, thermal resistance, chemical resistance, abrasion resistance, moisture barriers, and oxygen barriers. Highly transparent multilayer barrier coatings have also been developed to protect sensitive materials from damage due to water vapor. The water sensitive materials can be electronic components such as organic, inorganic, and hybrid organic/inorganic semiconductor devices. The multilayer barrier coatings can be deposited directly on the sensitive material, or can be deposited on a flexible transparent substrate such as a (co)polymer film.

Multilayer barrier coatings can be prepared by a variety of production methods. These methods include liquid coating techniques such as solution coating, roll coating, dip coating, spray coating, spin coating; and dry coating techniques such as Chemical Vapor Deposition (CVD), Plasma Enhanced Chemical Vapor Deposition (PECVD), sputtering and vacuum processes for thermal evaporation of solid materials. One approach for multilayer barrier coatings has been to produce multilayer oxide coatings, such as aluminum oxide or silicon oxide, interspersed with thin (co)polymer film protective layers. Each oxide/(co)polymer film pair is often referred to as a "dyad", and the alternating oxide/(co)polymer multilayer construction can contain several dyads to provide adequate protection from moisture and oxygen. Examples of such transparent multilayer barrier coatings and processes can be found, for example, in U.S. Pat. No. 5,440,446 (Shaw et al.); U.S. Pat. No. 5,877,895 (Shaw et al.); U.S. Pat. No. 6,010,751 (Shaw et al.); U.S. Pat. No. 7,018,713 (Padiyath et al.); and U.S. Pat. No. 6,413,645 (Graff et al.).

SUMMARY

In one aspect, the present disclosure describes an article including a substrate selected from a (co)polymeric film or an electronic device, the electronic device further including an organic light emitting device (OLED), an electrophoretic light emitting device, a liquid crystal display, a thin film transistor, a photovoltaic device, or a combination thereof; a base (co)polymer layer on a major surface of the substrate; an oxide layer on the base (co)polymer layer; and a protective (co)polymer layer on the oxide layer, wherein the protective (co)polymer layer includes the reaction product of at least one urethane (multi)-(meth) acrylate (multi)-silane precursor compound of the formula $R_S$—N(H)—C(O)—O—$R_A$ or $R_S$—O—C(O)—N(H)—$R_A$. $R_S$ is a silane containing group of the formula —$R^1$—[Si($Y_p$)($R^2$)$_{3-p}$]$_q$, in which $R^1$ is a multivalent alkylene, arylene, alkarylene, or aralkylene group, said alkylene, arylene, alkarylene, or aralkylene groups optionally containing one or more catenary oxygen atoms, each Y is a hydrolysable group, $R^2$ is a monovalent alkyl or aryl group; p is 1, 2, or 3, and q is 1-5. $R_A$ is a (meth)acryl group containing group of the formula $R^{11}$-(A)$_n$, in which $R^{11}$ is a polyvalent alkylene, arylene, alkarylene, or aralkylene group, said alkylene, arylene, alkarylene, or aralkylene groups optionally containing one or more catenary oxygen atoms, A is a (meth)acryl group comprising the formula $X^2$—C(O)—C($R^3$)=$CH_2$, in which $X^2$ is —O, —S, or —$NR^3$, $R^3$ is H, or $C_1$-$C_4$, and n=1 to 5.

In any of the foregoing embodiments, each hydrolysable group Y is independently selected from an alkoxy group, an acetate group, an aryloxy group, and a halogen. In some particular exemplary embodiments of the foregoing articles, at least some of the hydrolysable groups Y are alkoxy groups.

In additional exemplary embodiments of any of the foregoing articles, the article includes a multiplicity of alternating layers of the oxide layer and the protective (co)polymer layer on the base (co)polymer layer. In other exemplary embodiments of any of the foregoing articles, the base (co)polymer layer includes a (meth)acrylate smoothing layer.

In further exemplary embodiments of any of the foregoing articles, the oxide layer includes at least one oxide, nitride, carbide or boride of atomic elements selected from Groups IIA, IIIA, IVA, VA, VIA, VIIA, IB, or IIB, metals of Groups IIIB, IVB, or VB, rare-earth metals, or a combination or mixture thereof. In some exemplary embodiments of any of the foregoing articles, the article further includes an oxide layer applied to the protective (co)polymer layer, optionally wherein the oxide layer includes silicon aluminum oxide.

Some exemplary embodiments of the present disclosure provide composite barrier assemblies, for example composite barrier films. Thus, in some exemplary embodiments of composite barrier films, the substrate includes a flexible transparent (co)polymeric film, optionally wherein the substrate comprises polyethylene terephthalate (PET), polyethylene napthalate (PEN), heat stabilized PET, heat stabilized PEN, polyoxymethylene, polyvinylnaphthalene, polyetheretherketone, a fluoro(co)polymer, polycarbonate, polymethylmethacrylate, poly α-methyl styrene, polysulfone, polyphenylene oxide, polyetherimide, polyethersulfone, polyamideimide, polyimide, polyphthalamide, or combinations thereof. In a further aspect, the disclosure describes methods of using a composite film as described above in an article selected from a photovoltaic device, a solid state lighting device, a display device, and combinations thereof. Exemplary solid state lighting devices include semiconductor light-emitting diodes (SLEDs, more commonly known as LEDs), organic light-emitting diodes (OLEDs), or polymer light-emitting diodes (PLEDs). Exemplary display devices include liquid crystal displays, OLED displays, and quantum dot displays.

In an additional aspect, the disclosure describes a process including (a) applying a base (co)polymer layer to a major surface of a substrate, (b) applying an oxide layer on the base (co)polymer layer, and (c) depositing on the oxide layer a protective (co)polymer layer, wherein the protective (co) polymer layer includes a (co)polymer formed as the reaction product of at least one of the foregoing urethane (multi)-(meth)acrylate (multi)-silane precursor compounds of the formula $R_S$—N(H)—C(O)—O—$R_A$ or $R_S$—O—C(O)—N(H)—$R_A$, as previously described. The substrate is selected from a (co)polymeric film or an electronic device, the electronic device further including an organic light emitting device (OLED), an electrophoretic light emitting device, a liquid crystal display, a thin film transistor, a photovoltaic device, or a combination thereof.

In some exemplary embodiments of the process, the at least one urethane (multi)-(meth)acrylate (multi)-silane precursor compound undergoes a chemical reaction to form the protective (co)polymer layer at least in part on the oxide layer. Optionally, the chemical reaction is selected from a free radical polymerization reaction, and a hydrolysis reaction. In any of the foregoing articles, each hydrolysable group Y is independently selected from an alkoxy group, an acetate group, an aryloxy group, and a halogen. In some particular exemplary embodiments of the foregoing articles, at least some of the hydrolysable groups Y are alkoxy groups.

In some particular exemplary embodiments of any of the foregoing processes, step (a) includes (i) evaporating a base (co)polymer precursor, (ii) condensing the evaporated base (co)polymer precursor onto the substrate, and (iii) curing the evaporated base (co)polymer precursor to form the base (co)polymer layer. In certain such exemplary embodiments, the base (co)polymer precursor includes a (meth)acrylate monomer.

In certain particular exemplary embodiments of any of the foregoing processes, step (b) includes depositing an oxide onto the base (co)polymer layer to form the oxide layer. Depositing is achieved using sputter deposition, reactive sputtering, chemical vapor deposition, or a combination thereof. In some particular exemplary embodiments of any of the foregoing processes, step (b) includes applying a layer of an inorganic silicon aluminum oxide to the base (co) polymer layer. In further exemplary embodiments of any of the foregoing processes, the process further includes sequentially repeating steps (b) and (c) to form a multiplicity of alternating layers of the protective (co)polymer layer and the oxide layer on the base (co)polymer layer.

In additional exemplary embodiments of any of the foregoing processes, step (c) further includes at least one of co-evaporating the at least one urethane (multi)-(meth) acrylate (multi)-silane precursor compound with a (meth) acrylate compound from a liquid mixture, or sequentially evaporating the at least one urethane (multi)-(meth)acrylate (multi)-silane precursor compound and a (meth)acrylate compound from separate liquid sources. Optionally, the liquid mixture includes no more than about 10 wt. % of the urethane (multi)-(meth)acrylate (multi)-silane precursor compound. In further exemplary embodiments of such processes, step (c) further includes at least one of co-condensing the urethane (multi)-(meth)acrylate (multi)-silane precursor compound with the (meth)acrylate compound onto the oxide layer, or sequentially condensing the urethane (multi)-(meth)acrylate (multi)-silane precursor compound and the (meth)acrylate compound on the oxide layer.

In further exemplary embodiments of any of the foregoing processes, reacting the urethane (multi)-(meth)acrylate (multi)-silane precursor compound with the (meth)acrylate compound to form a protective (co)polymer layer on the oxide layer occurs at least in part on the oxide layer.

Some exemplary embodiments of the present disclosure provide composite barrier assemblies, articles or barrier films which exhibit improved moisture resistance when used in moisture exposure applications. Exemplary embodiments of the disclosure can enable the formation of barrier assemblies, articles or barrier films that exhibit superior mechanical properties such as elasticity and flexibility yet still have low oxygen or water vapor transmission rates.

Exemplary embodiments of barrier assemblies or barrier films according to the present disclosure are preferably transmissive to both visible and infrared light. Exemplary embodiments of barrier assemblies or barrier films according to the present disclosure are also typically flexible. Exemplary embodiments of barrier assemblies or barrier films according to the present disclosure generally do not exhibit delamination or curl that can arise from thermal stresses or shrinkage in a multilayer structure. The properties of exemplary embodiments of barrier assemblies or barrier films disclosed herein typically are maintained even after high temperature and humidity aging.

Various aspects and advantages of exemplary embodiments of the present disclosure have been summarized. The above Summary is not intended to describe each illustrated embodiment or every implementation of the present invention. Further features and advantages are disclosed in the embodiments that follow. The Drawings and the Detailed Description that follow more particularly exemplify certain preferred embodiments using the principles disclosed herein.

BRIEF DESCRIPTION OF THE DRAWINGS

The accompanying drawings are incorporated in and constitute a part of this specification and, together with the description, explain the advantages and principles of exemplary embodiments of the present disclosure.

Like reference numerals in the drawings indicate like elements. The drawings herein are not drawn to scale, and in the drawings, the illustrated elements are sized to emphasize selected features.

DETAILED DESCRIPTION

Glossary

Figure 1:
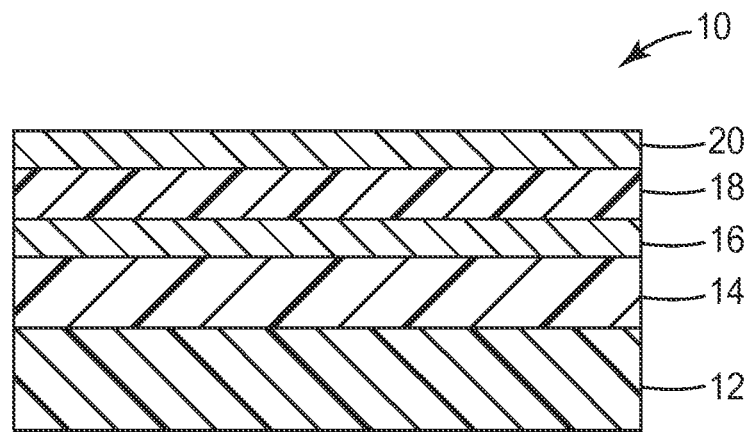
FIG. 1 is a diagram illustrating an exemplary moisture-resistant barrier assembly in an article or film having a vapor-deposited adhesion-promoting coating according to an exemplary embodiment of the present disclosure.

Certain terms are used throughout the description and the claims that, while for the most part are well known, may require some explanation. It should understood that, as used herein, The words "a", "an", and "the" are used interchangeably with "at least one" to mean one or more of the elements being described.

By using words of orientation such as "atop", "on", "covering", "uppermost", "underlying" and the like for the location of various elements in the disclosed coated articles, we refer to the relative position of an element with respect to a horizontally-disposed, upwardly-facing substrate. It is not intended that the substrate or articles should have any particular orientation in space during or after manufacture.

By using the term "overcoated" to describe the position of a layer with respect to a substrate or other element of a barrier assembly in an article or film of the disclosure, we refer to the layer as being atop the substrate or other element, but not necessarily contiguous to either the substrate or the other element.

By using the term "separated by" to describe the position of a (co)polymer layer with respect to two inorganic barrier layers, we refer to the (co)polymer layer as being between the inorganic barrier layers but not necessarily contiguous to either inorganic barrier layer.

The terms "barrier assembly," "barrier film" or "barrier layer" refers to an assembly, film or layer which is designed to be impervious to vapor, gas or aroma migration. Exemplary gases and vapors that may be excluded include oxygen and/or water vapor.

The term "(meth)acrylate" with respect to a monomer, oligomer or compound means a vinyl-functional alkyl ester formed as the reaction product of an alcohol with an acrylic or a methacrylic acid.

The term "polymer" or "(co)polymer" includes homopolymers and copolymers, as well as homopolymers or copolymers that may be formed in a miscible blend, e.g., by coextrusion or by reaction, including, e.g., transesterification. The term "copolymer" includes both random and block copolymers.

The term "cure" refers to a process that causes a chemical change, e.g., a reaction via consumption of water, to solidify a film layer or increase its viscosity.

The term "cross-linked" (co)polymer refers to a (co)polymer whose (co)polymer chains are joined together by covalent chemical bonds, usually via cross-linking molecules or groups, to form a network (co)polymer. A cross-linked (co)polymer is generally characterized by insolubility, but may be swellable in the presence of an appropriate solvent.

The term "cured (co)polymer" includes both cross-linked and uncross-linked (co)polymers.

The term "$T_g$" refer to the glass transition temperature of a cured (co)polymer when evaluated in bulk rather than in a thin film form. In instances where a (co)polymer can only be examined in thin film form, the bulk form $T_g$ can usually be estimated with reasonable accuracy. Bulk form $T_g$ values usually are determined by evaluating the rate of heat flow vs. temperature using differential scanning calorimetry (DSC) to determine the onset of segmental mobility for the (co)polymer and the inflection point (usually a second-order transition) at which the (co)polymer can be said to change from a glassy to a rubbery state. Bulk form $T_g$ values can also be estimated using a dynamic mechanical thermal analysis (DMTA) technique, which measures the change in the modulus of the (co)polymer as a function of temperature and frequency of vibration.

By using the term "visible light-transmissive" support, layer, assembly or device, we mean that the support, layer, assembly or device has an average transmission over the visible portion of the spectrum, $T_{vis}$, of at least about 20%, measured along the normal axis.

The term "metal" includes a pure metal (i.e. a metal in elemental form such as, for example silver, gold, platinum, and the like) or a metal alloy.

The term "vapor coating" or "vapor depositing" means applying a coating to a substrate surface from a vapor phase, for example, by evaporating and subsequently depositing onto the substrate surface a precursor material to the coating or the coating material itself Exemplary vapor coating processes include, for example, physical vapor deposition (PVD), chemical vapor deposition (CVD), and combinations thereof.

Various exemplary embodiments of the disclosure will now be described with particular reference to the Drawings. Exemplary embodiments of the present disclosure may take on various modifications and alterations without departing from the spirit and scope of the disclosure. Accordingly, it is to be understood that the embodiments of the present disclosure are not to be limited to the following described exemplary embodiments, but are to be controlled by the limitations set forth in the claims and any equivalents thereof.

Identification of a Problem to be Solved

Flexible barrier assemblies, coatings or barrier films are desirable for electronic devices whose components are sensitive to the ingress of water vapor. A multilayer barrier assembly, coating or film may provide advantages over glass as it is flexible, light-weight, durable, and enables low cost continuous roll-to-roll processing.

Each of the known methods for producing a multilayer barrier assembly, coating or film has limitations. Chemical deposition methods (CVD and PECVD) form vaporized metal alkoxide precursors that undergo a reaction, when adsorbed on a substrate, to form inorganic coatings. These processes are generally limited to low deposition rates (and consequently low line speeds), and make inefficient use of the alkoxide precursor (much of the alkoxide vapor is not incorporated into the coating). The CVD process also requires high substrate temperatures, often in the range of 300-500° C., which may not be suitable for (co)polymer substrates.

Vacuum processes such as thermal evaporation of solid materials (e.g., resistive heating or e-beam heating) also provide low metal oxide deposition rates. Thermal evaporation is difficult to scale up for roll wide web applications requiring very uniform coatings (e.g., optical coatings) and can require substrate heating to obtain quality coatings. Additionally, evaporation/sublimation processes can require ion-assist, which is generally limited to small areas, to improve the coating quality.

Sputtering has also been used to form metal oxide layers. While the deposition energy of the sputter process used for forming the barrier oxide layer is generally high, the energy involved in depositing the (meth)acrylate layers is generally low. As a result the (meth)acrylate layer typically does not have good adhesive properties with the layer below it, for example, an inorganic barrier oxide sub-layer. To increase the adhesion level of the protective (meth)acrylate layer to the barrier oxide, a thin sputtered layer of silicon sub-oxide is known to be useful in the art. If the silicon sub oxide layer is not included in the stack, the protective (meth)acrylate layer has poor initial adhesion to the barrier oxide. The silicon sub oxide layer sputter process must be carried out with precise power and gas flow settings to maintain adhesion performance. This deposition process has historically been susceptible to noise resulting in varied and low adhesion of the protective (meth)acrylate layer. It is therefore desirable to eliminate the need for a silicon sub oxide layer in the final barrier construct for increased adhesion robustness and reduction of process complexity.

Even when the "as deposited" adhesion of the standard barrier stack is initially acceptable, the sub oxide and protective (meth)acrylate layer has demonstrated weakness when exposed to accelerated aging conditions of 85° C./85% relative humidity (RH). This inter-layer weakness can result in premature delamination of the composite film from the devices it is intended to protect. It is desirable that the multi-layer construction improves upon and maintains initial adhesion levels when aged in 85° C. and 85% RH.

One solution to this problem is to use what is referred to as a "tie" layer of particular elements such chromium, zirconium, titanium, silicon and the like, which are often sputter deposited as a mono- or thin-layer of the material either as the element or in the presence of small amount of oxygen. The tie layer element can then form chemical bonds to both the substrate layer, an oxide, and the capping layer, a (co)polymer.

Tie layers are generally used in the vacuum coating industry to achieve adhesion between layers of differing materials. The process used to deposit the layers often requires fine tuning to achieve the right layer concentration of tie layer atoms. The deposition can be affected by slight variations in the vacuum coating process such as fluctuation in vacuum pressure, out-gassing, and cross contamination from other processes resulting in variation of adhesion levels in the product. In addition, tie layers often do not retain their initial adhesion levels after exposure to water vapor. A more robust solution for adhesion improvement in composite films is desirable.

Discovery of a Solution to the Problem

We have surprisingly discovered that a composite barrier assembly in an article or film comprising a protective (co)polymer layer comprising the reaction product of at least one urethane (multi)-(meth)acrylate (multi)-silane precursor compound as described further below, improves the adhesion and moisture barrier performance of a multilayer composite barrier assembly in an article or film. These multilayer composite barrier assembly in an article or films have a number of applications in the photovoltaic, display, lighting, and electronic device markets as flexible replacements for glass encapsulating materials.

In exemplary embodiments of the present disclosure, the desired technical effects and solution to the technical problem to obtain improved barrier assemblies in an article or film were obtained by chemically modifying the compositions used in the process for applying (e.g., by vapor coating) a protective (co)polymer layer to a multilayer composite barrier assembly in an article or film to achieve, in some exemplary embodiments:

1) a robust chemical bond with an inorganic oxide surface,
2) a robust chemical bond to the (meth)acrylate coating through (co)polymerization, and
3) the maintenance of some of the physical properties of the modified molecules (e.g., boiling point, vapor pressure, and the like) such that they can be co-evaporated with a bulk (meth)acrylate material.

Multilayer Composite Barrier Assemblies or Films

Thus, in exemplary embodiments, the disclosure describes a multilayer composite barrier assembly in an article or film, comprising a substrate, a base (co)polymer layer on a major surface of the substrate, an oxide layer on the base (co)polymer layer; and a protective (co)polymer layer on the oxide layer, the protective (co)polymer layer the reaction product of at least one wherein the protective (co)polymer layer comprises the reaction product of at least one urethane (multi)-(meth)acrylate (multi)-silane precursor compound of the formula $R_S$—N(H)—C(O)—O—$R_A$ or $R_S$—O—C(O)—N(H)—$R_A$, as described further below.

An optional inorganic layer, which preferably is an oxide layer, can be applied over the protective (co)polymer layer. Presently preferred inorganic layers comprise at least one of silicon aluminum oxide or indium tin oxide.

Turning to the drawings, FIG. 1 is a diagram of an exemplary barrier assembly in an article or film 10 having a moisture resistant coating comprising a single dyad, applied to a photovoltaic device 11. Film 10 includes layers arranged in the following order: a substrate 12; a base (co)polymer layer 14; an oxide layer 16; a protective (co)polymer layer 18 comprising the reaction product of at least one urethane (multi)-(meth)acrylate (multi)-silane precursor compound as described herein; and an optional oxide layer 20. Oxide layer 16 and protective (co)polymer layer 18 together form a dyad and, although only one dyad is shown, film 10 can include additional dyads of alternating oxide layer 16 and protective (co)polymer layer 18 between substrate 10 and the uppermost dyad.

In certain exemplary embodiments, the composite barrier assembly in an article or film comprises a plurality of alternating layers of the oxide layer and the protective (co)polymer layer on the base (co)polymer layer. The oxide layer and protective (co)polymer layer together form a "dyad", and in one exemplary embodiment, the barrier assembly in an article or film can include more than one dyad, forming a multilayer barrier assembly in an article or film. Each of the oxide layers and/or protective (co)polymer layers in the multilayer barrier assembly in an article or film (i.e. including more than one dyad) can be the same or different. An optional inorganic layer, which preferably is an oxide layer, can be applied over the plurality of alternating layers or dyads.

In some exemplary embodiments, protective (co)polymer layer 18 comprising the reaction product of at least one urethane (multi)-(meth)acrylate (multi)-silane precursor compound improves the moisture resistance of film 10 and the peel strength adhesion of protective (co)polymer layer 18 to the underlying oxide layer, leading to improved adhesion and delamination resistance within the further barrier stack layers, as explained further below. Presently preferred materials for use in the barrier assembly in an article or film 10 are also identified further below, and in the Examples.

Protective (Co)polymer Layers

The present disclosure describes protective (co)polymer layers used in barrier assemblies in articles or films (i.e. as barrier films) useful in reducing oxygen and/or water vapor barrier transmission when used as packaging materials, for example, to package electronic devices. Each protective (co)polymer layer includes in its manufacture at least one composition of matter described herein as a urethane (multi)-(meth)acrylate (multi)-silane precursor compound, the reaction product thereof forms a (co)polymer, as described further below. Among other things, urethane (multi)-(meth)acrylate (multi)-silane precursor compounds as disclosed herein are, in some exemplary embodiments, useful as coupling agents for improving the interlayer adhesion of multilayer barrier assembly in an article or films.

Composite Barrier Assembly or Barrier Film Materials

The present disclosure describes protective (co)polymer layers comprising the reaction product of at least one urethane (multi)-(meth)acrylate (multi)-silane precursor compounds, as described further below.

Urethane (Multi)-Acrylate-Silane Precursor Compound

In exemplary embodiments, the present disclosure uses compositions of matter comprising at least one urethane (multi)-(meth)acrylate (multi)-silane precursor compounds of the formula $R_S$—N(H)—C(O)—O—$R_A$ or $R_S$—O—C(O)—N(H)—$R_A$. $R_S$ is a silane containing group of the formula —$R^1$—$[Si(Y_p)(R^2)_{3-p}]_q$, in which $R^1$ is a multivalent alkylene, arylene, alkarylene, or aralkylene group, said alkylene, arylene, alkarylene, or aralkylene groups optionally containing one or more catenary oxygen atoms, each Y is a hydrolysable group, $R^2$ is a monovalent alkyl or aryl group; p is 1, 2, or 3, and q is 1-5. $R_A$ is a (meth)acryl group containing group of the formula $R^{11}$-$(A)_n$, in which $R^{11}$ is a polyvalent alkylene, arylene, alkarylene, or aralkylene group, said alkylene, arylene, alkarylene, or aralkylene groups optionally containing one or more catenary oxygen atoms, A is a (meth)acryl group comprising the formula $X^2$—C(O)—C($R^3$)=$CH_2$, in which $X^2$ is —O, —S, or —$NR^3$, $R^3$ is H, or $C_1$-$C_4$, and n=1 to 5.

In any of the foregoing embodiments, each hydrolysable group Y is independently selected from an alkoxy group, an acetate group, an aryloxy group, and a halogen. In some particular exemplary embodiments of the foregoing articles, at least some of the hydrolysable groups Y are alkoxy groups.

Urethane (multi)-(meth)acrylate-silane precursor compounds of the foregoing type are known, and are typically synthesized by reaction of (meth)acrylated materials having mono-alcohol functionality with silane compounds having mono-isocyanate functionality, either neat or in a solvent, and often with a catalyst, such as a tin compound, to accelerate the reaction. Alternatively these materials may be made by reaction of (meth)acrylated materials having mono-isocyanate functionality with silane compounds having mono-alcohol functionality, under similar conditions.

Examples of (meth)acrylated materials having alcohol functionality include hydroxyethyl acrylate, hydroxypropyl acrylate, hydroxybutyl acrylate, hydroxyethyl methacrylate, hydroxypropyl methacrylate, hydroxybutyl methacrylate, 1,3-dimethacryloxy-2-hydroxy-propane, 1-acryloxy-3-methacryloxy-2-hydroxy-propane, trimethylolpropane diacrylate, pentaetrythritol triacrylate.

Examples of silane compounds having isocyanate functionality include 3-triethoxysilylpropyl isocyanate, and 3-trimethoxysilylpropyl isocyanate. Some typical (meth)acrylated materials having mono-isocyanate functionality include 3-isocyanatoethyl methacrylate and 3-isocyanatoethyl methacrylate. Examples of silane compounds having mono-alcohol functionality include N-(hydroxyethyl)-N-methylaminopropyltrimethoxysilane, and 3-hydroxy-butyl-trimethoxysilane.

Typical preparations of urethanes can be found in Polyurethanes: Chemistry and Technology, Saunders and Frisch, Interscience Publishers (New York, 1963 (Part I) and 1964 (Part II).

The molecular weights of the urethane (multi)-(meth)acrylate (multi-silane precursor compounds are in the range where sufficient vapor pressure at vacuum process conditions is effective to carry out evaporation and then subsequent condensation to a thin liquid film. The molecular weights are preferably less than about 2,000 Da, more preferably less than 1,000 Da, even more preferably less than 500 Da.

Preferably, the urethane (multi)-(meth)acrylate (multi)-silane precursor compound is present at no more than 20% by weight (% wt.) of the vapor coated mixture; more preferably no more than 19%, 18%, 17%, 16%, 15%, 14%, 13%, 12%, 11%, and even more preferably 10%, 9%, 8%, 7%, 6%, 5%, 4%, 3%, 2% or even 1% wt. of the vapor deposited mixture.

Substrates

The substrate 12 is selected from a (co)polymeric film or an electronic device, the electronic device further including an organic light emitting device (OLED), an electrophoretic light emitting device, a liquid crystal display, a thin film transistor, a photovoltaic device, or a combination thereof.

Typically, the electronic device substrate is a moisture sensitive electronic device. The moisture sensitive electronic device can be, for example, an organic, inorganic, or hybrid organic/inorganic semiconductor device including, for example, a photovoltaic device such as a copper indium gallium (di)selenide (CIGS) solar cell; a display device such as an organic light emitting display (OLED), electrochromic display, electrophoretic display, or a liquid crystal display (LCD) such as a quantum dot LCD display; an OLED or other electroluminescent solid state lighting device, or combinations thereof and the like.

In some exemplary embodiments, substrate 12 can be a flexible, visible light-transmissive substrate, such as a flexible light transmissive (co)polymeric film. In one presently preferred exemplary embodiment, the substrates are substantially transparent, and can have a visible light transmission of at least about 50%, 60%, 70%, 80%, 90% or even up to about 100% at 550 nm.

Exemplary flexible light-transmissive substrates include thermoplastic (co)polymeric films including, for example, polyesters, polyacrylates (e.g., polymethyl methacrylate), polycarbonates, polypropylenes, high or low density polyethylenes, polysulfones, polyether sulfones, polyurethanes, polyamides, polyvinyl butyral, polyvinyl chloride, fluoro (co)polymers (e.g., polyvinylidene difluoride and polytetrafluoroethylene), polyethylene sulfide, and thermoset films such as epoxies, cellulose derivatives, polyimide, polyimide benzoxazole and polybenzoxazole.

Presently preferred (co)polymeric films comprise polyethylene terephthalate (PET), polyethylene napthalate (PEN), heat stabilized PET, heat stabilized PEN, polyoxymethylene, polyvinylnaphthalene, polyetheretherketone, fluoro(co)polymer, polycarbonate, polymethylmethacrylate, poly α-methyl styrene, polysulfone, polyphenylene oxide, polyetherimide, polyethersulfone, polyamideimide, polyimide, polyphthalamide, or combinations thereof.

In some exemplary embodiments, the substrate can also be a multilayer optical film ("MOF"), such as those described in U.S. Patent Application Publication No. US 2004/0032658 A1. In one exemplary embodiment, the films can be prepared on a substrate including PET.

The (co)polymeric film can be heat-stabilized, using heat setting, annealing under tension, or other techniques that will discourage shrinkage up to at least the heat stabilization temperature when the (co)polymeric film is not constrained.

The substrate may have a variety of thicknesses, e.g., about 0.01 to about 1 mm. The substrate may however be considerably thicker, for example, when a self-supporting article is desired. Such articles can conveniently also be made by laminating or otherwise joining a disclosed film made using a flexible substrate to a thicker, inflexible or less flexible supplemental support.

Base (Co)polymer Layer

Returning to FIG. 1, the base (co)polymer layer 14 can include any (co)polymer suitable for deposition in a thin film. In one aspect, for example, the base (co)polymer layer 14 can be formed from various precursors, for example, (meth)acrylate monomers and/or oligomers that include acrylates or methacrylates such as urethane acrylates, isobornyl acrylate, dipentaerythritol pentaacrylates, epoxy acrylates, epoxy acrylates blended with styrene, di-trimethylolpropane tetraacrylates, diethylene glycol diacrylates, 1,3-butylene glycol diacrylate, pentaacrylate esters, pentaerythritol tetraacrylates, pentaerythritol triacrylates, ethoxylated (3) trimethylolpropane triacrylates, ethoxylated (3) trimethylolpropane triacrylates, alkoxylated trifunctional acrylate esters, dipropylene glycol diacrylates, neopentyl glycol diacrylates, ethoxylated (4) bisphenol a dimethacrylates, cyclohexane dimethanol diacrylate esters, isobornyl methacrylate, cyclic diacrylates and tris (2-hydroxy ethyl) isocyanurate triacrylate, acrylates of the foregoing methacrylates and methacrylates of the foregoing acrylates. Preferably, the base (co)polymer precursor comprises a (meth) acrylate monomer.

The base (co)polymer layer 14 can be formed by applying a layer of a monomer or oligomer to the substrate and crosslinking the layer to form the (co)polymer in situ, e.g., by flash evaporation and vapor deposition of a radiation-crosslinkable monomer, followed by crosslinking using, for example, an electron beam apparatus, UV light source, electrical discharge apparatus or other suitable device. Coating efficiency can be improved by cooling the substrate.

The monomer or oligomer can also be applied to the substrate 12 using conventional coating methods such as roll coating (e.g., gravure roll coating) or spray coating (e.g., electrostatic spray coating), then crosslinked as set out above. The base (co)polymer layer 14 can also be formed by applying a layer containing an oligomer or (co)polymer in solvent and drying the thus-applied layer to remove the solvent. Plasma Enhanced Chemical Vapor Deposition (PECVD) may also be employed in some cases.

Most preferably, the base (co)polymer layer 14 is formed by flash evaporation and vapor deposition followed by crosslinking in situ, e.g., as described in U.S. Pat. No. 4,696,719 (Bischoff), U.S. Pat. No. 4,722,515 (Ham), U.S. Pat. No. 4,842,893 (Yializis et al.), U.S. Pat. No. 4,954,371 (Yializis), U.S. Pat. No. 5,018,048 (Shaw et al.), U.S. Pat. No. 5,032,461 (Shaw et al.), U.S. Pat. No. 5,097,800 (Shaw et al.), U.S. Pat. No. 5,125,138 (Shaw et al.), U.S. Pat. No. 5,440,446 (Shaw et al.), U.S. Pat. No. 5,547,908 (Furuzawa et al.), U.S. Pat. No. 6,045,864 (Lyons et al.), U.S. Pat. No. 6,231,939 (Shaw et al. and U.S. Pat. No. 6,214,422 (Yializis); in PCT International Publication No. WO 00/26973 (Delta V Technologies, Inc.); in D. G. Shaw and M. G. Langlois, "A New Vapor Deposition Process for Coating Paper and (co)polymer Webs", 6th International Vacuum Coating Conference (1992); in D. G. Shaw and M. G. Langlois, "A New High Speed Process for Vapor Depositing Acrylate Thin Films: An Update", Society of Vacuum Coaters 36th Annual Technical Conference Proceedings (1993); in D. G. Shaw and M. G. Langlois, "Use of Vapor Deposited Acrylate Coatings to Improve the Barrier Properties of Metallized Film", Society of Vacuum Coaters 37th Annual Technical Conference Proceedings (1994); in D. G. Shaw, M. Roehrig, M. G. Langlois and C. Sheehan, "Use of Evaporated Acrylate Coatings to Smooth the Surface of Polyester and Polypropylene Film Substrates", RadTech (1996); in J. Affinito, P. Martin, M. Gross, C. Coronado and E. Greenwell, "Vacuum Deposited Polymer/Metal Multilayer Films for Optical Application", Thin Solid Films 270, 43-48 (1995); and in J. D. Affinito, M. E. Gross, C. A. Coronado, G. L. Graff, E. N. Greenwell and P. M. Martin, "Polymer-Oxide Transparent Barrier Layers", Society of Vacuum Coaters 39th Annual Technical Conference Proceedings (1996).

In some exemplary embodiments, the smoothness and continuity of the base (co)polymer layer 14 (and also each oxide layer 16 and protective (co)polymer layer 18) and its adhesion to the underlying substrate or layer may be enhanced by appropriate pretreatment. Examples of a suitable pretreatment regimen include an electrical discharge in the presence of a suitable reactive or non-reactive atmosphere (e.g., plasma, glow discharge, corona discharge, dielectric barrier discharge or atmospheric pressure discharge); chemical pretreatment or flame pretreatment. These pretreatments help make the surface of the underlying layer more receptive to formation of the subsequently applied (co)polymeric (or inorganic) layer. Plasma pretreatment can be particularly useful.

In some exemplary embodiments, a separate adhesion promotion layer which may have a different composition than the base (co)polymer layer 14 may also be used atop the substrate or an underlying layer to improve adhesion. The adhesion promotion layer can be, for example, a separate (co)polymeric layer or a metal-containing layer such as a layer of metal, metal oxide, metal nitride or metal oxynitride. The adhesion promotion layer may have a thickness of a few nm (e.g., 1 or 2 nm) to about 50 nm, and can be thicker if desired.

The desired chemical composition and thickness of the base (co)polymer layer will depend in part on the nature and surface topography of the substrate. The thickness preferably is sufficient to provide a smooth, defect-free surface to which the subsequent oxide layer can be applied. For example, the base (co)polymer layer may have a thickness of a few nm (e.g., 2 or 3 nm) to about 5 micrometers, and can be thicker if desired.

As described elsewhere, the composite film can include the oxide layer deposited directly on a substrate that includes a moisture sensitive device, a process often referred to as direct encapsulation. The moisture sensitive device can be, for example, an organic, inorganic, or hybrid organic/inorganic semiconductor device including, for example, a photovoltaic device such as a copper indium gallium di-selenide (CIGS) photovoltaic device; a display device such as an organic light emitting diode (OLED), electrochromic, or an electrophoretic display; an OLED or other electroluminescent solid state lighting device, or others. Flexible electronic devices can be encapsulated directly with the gradient composition oxide layer. For example, the devices can be attached to a flexible carrier substrate, and a mask can be deposited to protect electrical connections from the oxide layer deposition. The base (co)polymer layer 14, the oxide layer 16 and the protective (co)polymer layer 18 can be deposited as described further below, and the mask can then be removed, exposing the electrical connections.

Oxide Layers

The improved composite film includes at least one oxide layer 16. The oxide layer preferably comprises at least one inorganic material. Suitable inorganic materials include oxides, nitrides, carbides or borides of different atomic elements. Presently preferred inorganic materials included in the oxide layer comprise oxides, nitrides, carbides or borides of atomic elements from Groups IIA, IIIA, IVA, VA, VIA, VIIA, IB, or IIB, metals of Groups IIIB, IVB, or VB, rare-earth metals, or combinations thereof. In some particular exemplary embodiments, an inorganic layer, more preferably an inorganic oxide layer, may be applied to the uppermost protective (co)polymer layer. Preferably, the oxide layer comprises silicon aluminum oxide or indium tin oxide.

In some exemplary embodiments, the composition of the oxide layer may change in the thickness direction of the layer, i.e. a gradient composition. In such exemplary embodiments, the oxide layer preferably includes at least two inorganic materials, and the ratio of the two inorganic materials changes throughout the thickness of the oxide layer. The ratio of two inorganic materials refers to the relative proportions of each of the inorganic materials. The ratio can be, for example, a mass ratio, a volume ratio, a concentration ratio, a molar ratio, a surface area ratio, or an atomic ratio.

The resulting gradient oxide layer is an improvement over homogeneous, single component layers. Additional benefits in barrier and optical properties can also be realized when combined with thin, vacuum deposited protective (co)polymer layers. A multilayer gradient inorganic-(co)polymer barrier stack can be made to enhance optical properties as well as barrier properties.

The composite film can be fabricated by deposition of the various layers onto the substrate, in a roll-to-roll vacuum chamber similar to the system described in U.S. Pat. No. 5,440,446 (Shaw et al.) and U.S. Pat. No. 7,018,713 (Padiyath, et al.). The deposition of the layers can be in-line, and in a single pass through the system. In some cases, the composite film can pass through the system several times, to form a multilayer composite film having several dyads.

The first and second inorganic materials can be oxides, nitrides, carbides or borides of metal or nonmetal atomic elements, or combinations of metal or nonmetal atomic elements. By "metal or nonmetal" atomic elements is meant atomic elements selected from the periodic table Groups HA, IIIA, IVA, VA, VIA, VIIA, IB, or IIB, metals of Groups IIIB, IVB, or VB, rare-earth metals, or combinations thereof. Suitable inorganic materials include, for example, metal oxides, metal nitrides, metal carbides, metal oxynitrides, metal oxyborides, and combinations thereof, e.g., silicon oxides such as silica, aluminum oxides such as alumina, titanium oxides such as titania, indium oxides, tin oxides, indium tin oxide ("ITO"), tantalum oxide, zirconium oxide, niobium oxide, aluminum nitride, silicon nitride, boron nitride, aluminum oxynitride, silicon oxynitride, boron oxynitride, zirconium oxyboride, titanium oxyboride, and combinations thereof. ITO is an example of a special class of ceramic materials that can become electrically conducting with the proper selection of the relative proportions of each elemental constituent. Silicon-aluminum oxide and indium tin oxide are presently preferred inorganic materials forming the oxide layer 16.

For purposes of clarity, the oxide layer 16 described in the following discussion is directed toward a composition of oxides; however, it is to be understood that the composition can include any of the oxides, nitrides, carbides, borides, oxynitrides, oxyborides and the like described above.

In one embodiment of the oxide layer 16, the first inorganic material is silicon oxide, and the second inorganic material is aluminum oxide. In this embodiment, the atomic ratio of silicon to aluminum changes throughout the thickness of the oxide layer, e.g., there is more silicon than aluminum near a first surface of the oxide layer, gradually becoming more aluminum than silicon as the distance from the first surface increases. In one embodiment, the atomic ratio of silicon to aluminum can change monotonically as the distance from the first surface increases, i.e., the ratio either increases or decreases as the distance from the first surface increases, but the ratio does not both increase and decrease as the distance from the first surface increases.

In another embodiment, the ratio does not increase or decrease monotonically, i.e. the ratio can increase in a first portion, and decrease in a second portion, as the distance from the first surface increases. In this embodiment, there can be several increases and decreases in the ratio as the distance from the first surface increases, and the ratio is non-monotonic. A change in the inorganic oxide concentration from one oxide species to another throughout the thickness of the oxide layer 16 results in improved barrier performance, as measured by water vapor transmission rate.

In addition to improved barrier properties, the gradient composition can be made to exhibit other unique optical properties while retaining improved barrier properties. The gradient change in composition of the layer produces corresponding change in refractive index through the layer. The materials can be chosen such that the refractive index can change from high to low, or vice versa. For example, going from a high refractive index to a low refractive index can allow light traveling in one direction to easily pass through the layer, while light travelling in the opposite direction may be reflected by the layer. The refractive index change can be used to design layers to enhance light extraction from a light emitting device being protected by the layer. The refractive index change can instead be used to pass light through the layer and into a light harvesting device such as a solar cell. Other optical constructions, such as band pass filters, can also be incorporated into the layer while retaining improved barrier properties.

In order to promote silane bonding to the oxide surface, it may be desirable to form hydroxyl silanol (Si—OH) groups on a freshly sputter deposited silicon dioxide ($SiO_2$) layer. The amount of water vapor present in a multi-process vacuum chamber can be controlled sufficiently to promote the formation of Si—OH groups in high enough surface concentration to provide increased bonding sites. With residual gas monitoring and the use of water vapor sources the amount of water vapor in a vacuum chamber can be controlled to ensure adequate generation of Si—OH groups.

Process for Making Articles Including Barrier Assemblies or Barrier Films

In other exemplary embodiments, the disclosure describes a process, e.g. for making a barrier film on a (co)polymer film substrate or for making an article by depositing a multilayer composite barrier assembly on an electronic device substrate, the process comprising: (a) applying a base (co)polymer layer to a major surface of a substrate, (b) applying an oxide layer on the base (co)polymer layer, and (c) depositing on the oxide layer a protective (co)polymer layer, wherein the protective (co)polymer layer includes a (co)polymer formed as the reaction product of at least one of the foregoing urethane (multi)-(meth)acrylate (multi)-silane precursor compounds of the formula $R_S$—N(H)—C(O)—O—$R_A$ or $R_S$—O—C(O)—N(H)—$R_A$, as previously described.

In some exemplary embodiments of the process, the at least one urethane (multi)-(meth)acrylate (multi)-silane precursor compound undergoes a chemical reaction to form the protective (co)polymer layer at least in part on the oxide layer. Optionally, the chemical reaction is selected from a free radical polymerization reaction, and a hydrolysis reaction. In any of the foregoing articles, each hydrolysable group Y is independently selected from an alkoxy group, an acetate group, an aryloxy group, and a halogen. In some particular exemplary embodiments of the foregoing articles, at least some of the hydrolysable groups Y are alkoxy groups.

In certain particular exemplary embodiments of any of the foregoing processes, step (b) includes depositing an oxide onto the base (co)polymer layer to form the oxide layer. Depositing is achieved using sputter deposition, reactive sputtering, chemical vapor deposition, or a combination thereof. In some particular exemplary embodiments of any of the foregoing processes, step (b) includes applying a layer of an inorganic silicon aluminum oxide to the base (co)polymer layer. In further exemplary embodiments of any of the foregoing processes, the process further includes sequentially repeating steps (b) and (c) to form a multiplicity of alternating layers of the protective (co)polymer layer and the oxide layer on the base (co)polymer layer.

In additional exemplary embodiments of any of the foregoing processes, reacting the urethane (multi)-(meth)acrylate (multi)-silane precursor compound with the (meth)acrylate compound to form a protective (co)polymer layer on the oxide layer occurs at least in part on the oxide layer.

It is presently preferred that the base polymer layer 14 is formed by flash evaporation and vapor deposition followed by crosslinking in situ, e.g., as described in U.S. Pat. No. 4,696,719 (Bischoff), U.S. Pat. No. 4,722,515 (Ham), U.S. Pat. No. 4,842,893 (Yializis et al.), U.S. Pat. No. 4,954,371 (Yializis), U.S. Pat. No. 5,018,048 (Shaw et al.), U.S. Pat. No. 5,032,461(Shaw et al.), U.S. Pat. No. 5,097,800 (Shaw et al.), U.S. Pat. No. 5,125,138 (Shaw et al.), U.S. Pat. No. 5,440,446 (Shaw et al.), U.S. Pat. No. 5,547,908 (Furuzawa et al.), U.S. Pat. No. 6,045,864 (Lyons et al.), U.S. Pat. No. 6,231,939 (Shaw et al. and U.S. Pat. No. 6,214,422 (Yializis); and in PCT International Publication No. WO 00/26973 (Delta V Technologies, Inc.).

As described above, the barrier assembly can be deposited directly on a (co)polymer film substrate, or a substrate that includes a moisture sensitive device, a process often referred to as direct deposition or direct encapsulation. Exemplary direct deposition processes and barrier assemblies or described in U.S. Pat. No. 5,654,084 (Affinito); U.S. Pat. No. 6,522,067 (Graff et al.); U.S. Pat. No. 6,548,912 (Graff et al.); U.S. Pat. No. 6,573,652 (Graff et al.); and U.S. Pat. No. 6,835,950 (Brown et al.).

In some exemplary embodiments, flexible electronic devices can be encapsulated directly with the methods described herein. For example, the devices can be attached to a flexible carrier substrate, and a mask can be deposited to protect electrical connections from the inorganic layer(s), (co)polymer layer(s), or other layer(s)s during their deposition. The inorganic layer(s), (co)polymeric layer(s), and other layer(s) making up the multilayer barrier assembly can be deposited as described elsewhere in this disclosure, and the mask can then be removed, exposing the electrical connections.

In one exemplary direct deposition or direct encapsulation embodiment, the moisture sensitive device is a moisture sensitive electronic device. The moisture sensitive electronic device can be, for example, an organic, inorganic, or hybrid organic/inorganic semiconductor device including, for example, a photovoltaic device such as a copper indium gallium (di)selenide (CIGS) solar cell; a display device such as an organic light emitting display (OLED), electrochromic display, electrophoretic display, or a liquid crystal display (LCD) such as a quantum dot LCD display; an OLED or other electroluminescent solid state lighting device, or combinations thereof and the like.

Examples of suitable processes for making a multilayer barrier assembly and suitable transparent multilayer barrier coatings can be found, for example, in U.S. Pat. No. 5,440,446 (Shaw et al.); U.S. Pat. No. 5,877,895 (Shaw et al.); U.S. Pat. No. 6,010,751 (Shaw et al.); and U.S. Pat. No. 7,018,713 (Padiyath et al.). In one presently preferred embodiment, the barrier assembly in an article or film can be fabricated by deposition of the various layers onto the substrate, in a roll-to-roll vacuum chamber similar to the system described in U.S. Pat. No. 5,440,446 (Shaw et al.) and U.S. Pat. No. 7,018,713 (Padiyath, et al.).

In one exemplary presently preferred embodiment, the disclosure describes a process for making a barrier assembly in an article or film, the process comprising: (a) vapor depositing and curing a base (co)polymer layer onto a major surface of a substrate; (b) vapor depositing an oxide layer on the base (co)polymer layer; and (c) vapor depositing and curing onto the oxide layer a protective (co)polymer layer, the protective (co)polymer layer comprising a (co)polymer formed as the reaction product of at least one of the foregoing urethane (multi)-(meth)acrylate (multi)-silane precursor compound of the formula $R_S$—N(H)—C(O)—O—$R_A$ or $R_S$—O—C(O)—N(H)—$R_A$, as previously described.

In some particular presently preferred exemplary embodiments of any of the foregoing processes, step (a) includes (i) evaporating a base (co)polymer precursor, (ii) condensing the evaporated base (co)polymer precursor onto the substrate, and (iii) curing the evaporated base (co)polymer precursor to form the base (co)polymer layer. In certain such exemplary embodiments, the base (co)polymer precursor includes a (meth)acrylate monomer.

In additional exemplary presently preferred embodiments of any of the foregoing processes, step (c) further includes at least one of co-evaporating the at least one urethane (multi)-(meth)acrylate (multi)-silane precursor compound with a (meth)acrylate compound from a liquid mixture, or sequentially evaporating the at least one urethane (multi)-(meth)acrylate (multi)-silane precursor compound and a (meth)acrylate compound from separate liquid sources. Optionally, the liquid mixture includes no more than about 10 wt. % of the urethane (multi)-(meth)acrylate (multi)-silane precursor compound.

In further exemplary presently preferred embodiments of such processes, step (c) further includes at least one of co-condensing the urethane (multi)-(meth)acrylate (multi)-silane precursor compound with the (meth)acrylate compound onto the oxide layer, or sequentially condensing the urethane (multi)-(meth)acrylate (multi)-silane precursor compound and the (meth)acrylate compound on the oxide layer.

The vapor deposition process is generally limited to compositions that are pumpable (liquid-phase with an acceptable viscosity); that can be atomized (form small droplets of liquid), flash evaporated (high enough vapor pressure under vacuum conditions), condensable (vapor pressure, molecular weight), and can be cross-linked in vacuum (molecular weight range, reactivity, functionality).

Figure 2:
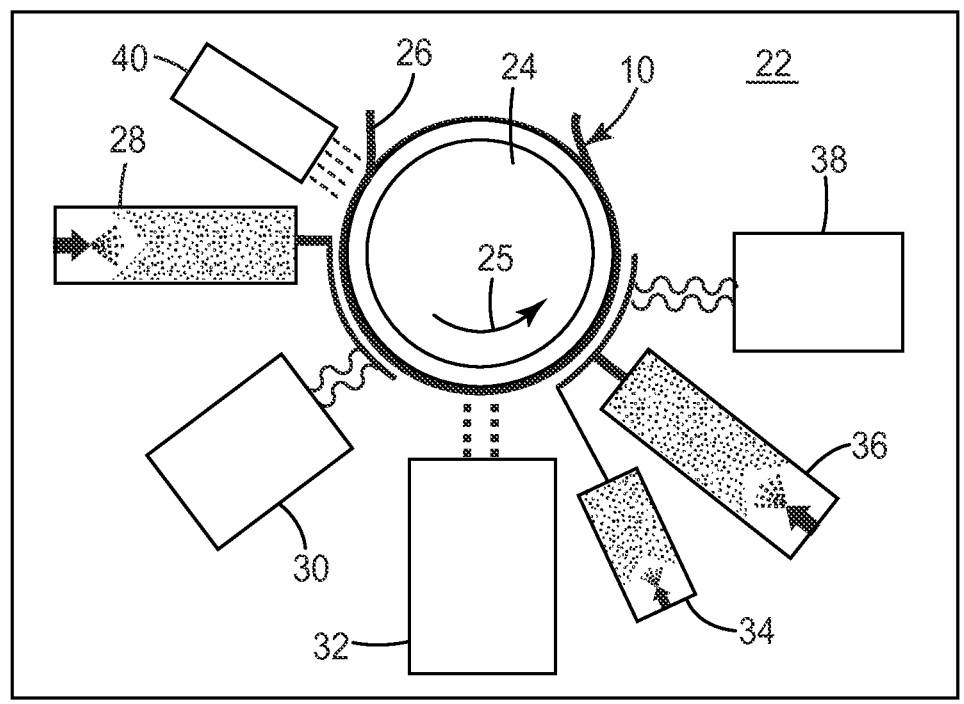
FIG. 2 is a diagram illustrating an exemplary process and apparatus for making a composite film according to an exemplary embodiment of the present disclosure.

FIG. 2 is a diagram of a system 22, illustrating an exemplary process for making composite film 10. System 22 is contained within an inert environment and includes a chilled drum 24 for receiving and moving the substrate 12 (FIG. 1), as represented by a film 26, thereby providing a moving web on which to form the barrier layers. Preferably, an optional nitrogen plasma treatment unit 40 may be used to plasma treat or prime film 26 in order to improve adhesion of the base (co)polymer layer 14 (FIG. 1) to substrate 12 (FIG. 1). An evaporator 28 applies a base (co)polymer precursor, which is cured by curing unit 30 to form base (co)polymer layer 14 (FIG. 1) as drum 24 advances the film 26 in a direction shown by arrow 25. An oxide sputter unit 32 applies an oxide to form layer 16 (FIG. 1) as drum 24 advances film 26.

For additional alternating oxide layers 16 and protective (co)polymer layers 18, drum 24 can rotate in a reverse direction opposite arrow 25 and then advance film 26 again to apply the additional alternating base (co)polymer and oxide layers, and that sub-process can be repeated for as many alternating layers as desired or needed. Once the base (co)polymer and oxide are complete, drum 24 further advances the film, and evaporator 36 deposits at least one urethane (multi)-(meth)acrylate (multi)-silane precursor compound, as described above, on oxide layer 16 to form protective (co)polymer layer 18 (FIG. 1). In certain presently preferred embodiments, reacting the urethane (multi)-(meth)acrylate (multi)-silane precursor compound to form a protective (co)polymer layer 18 on the oxide layer 16 occurs at least in part on the oxide layer 16.

Optional evaporator 34 may be used additionally to provide other co-reactants or co-monomers (e.g. additional protective (co)polymers) which may be useful in forming the protective (co)polymer layer 18 (FIG. 1). For additional alternating oxide layers 16 and protective (co)polymer layers 18, drum 24 can rotate in a reverse direction opposite arrow 25 and then advance film 26 again to apply the additional alternating oxide layers 16 and protective (co) polymer layers 18, and that sub-process can be repeated for as many alternating layers or dyads as desired or needed.

The oxide layer 16 can be formed using techniques employed in the film metalizing art such as sputtering (e.g., cathode or planar magnetron sputtering), evaporation (e.g., resistive or electron beam evaporation), chemical vapor deposition, plating and the like. In one aspect, the oxide layer 16 is formed using sputtering, e.g., reactive sputtering. Enhanced barrier properties have been observed when the oxide layer is formed by a high energy deposition technique such as sputtering compared to lower energy techniques such as conventional chemical vapor deposition processes. Without being bound by theory, it is believed that the enhanced properties are due to the condensing species arriving at the substrate with greater kinetic energy as occurs in sputtering, leading to a lower void fraction as a result of compaction.

In some exemplary embodiments, the sputter deposition process can use dual targets powered by an alternating current (AC) power supply in the presence of a gaseous atmosphere having inert and reactive gasses, for example argon and oxygen, respectively. The AC power supply alternates the polarity to each of the dual targets such that for half of the AC cycle one target is the cathode and the other target is the anode. On the next cycle the polarity switches between the dual targets. This switching occurs at a set frequency, for example about 40 kHz, although other frequencies can be used. Oxygen that is introduced into the process forms oxide layers on both the substrate receiving the inorganic composition, and also on the surface of the target. The dielectric oxides can become charged during sputtering, thereby disrupting the sputter deposition process. Polarity switching can neutralize the surface material being sputtered from the targets, and can provide uniformity and better control of the deposited material.

In further exemplary embodiments, each of the targets used for dual AC sputtering can include a single metal or nonmetal element, or a mixture of metal and/or nonmetal elements. A first portion of the oxide layer closest to the moving substrate is deposited using the first set of sputtering targets. The substrate then moves proximate the second set of sputtering targets and a second portion of the oxide layer is deposited on top of the first portion using the second set of sputtering targets. The composition of the oxide layer changes in the thickness direction through the layer.

In additional exemplary embodiments, the sputter deposition process can use targets powered by direct current (DC) power supplies in the presence of a gaseous atmosphere having inert and reactive gasses, for example argon and oxygen, respectively. The DC power supplies supply power (e.g. pulsed power) to each cathode target independent of the other power supplies. In this aspect, each individual cathode target and the corresponding material can be sputtered at differing levels of power, providing additional control of composition through the layer thickness. The pulsing aspect of the DC power supplies is similar to the frequency aspect in AC sputtering, allowing control of high rate sputtering in the presence of reactive gas species such as oxygen. Pulsing DC power supplies allow control of polarity switching, can neutralize the surface material being sputtered from the targets, and can provide uniformity and better control of the deposited material.

In one particular exemplary embodiment, improved control during sputtering can be achieved by using a mixture, or atomic composition, of elements in each target, for example a target may include a mixture of aluminum and silicon. In another embodiment, the relative proportions of the elements in each of the targets can be different, to readily provide for a varying atomic ratio throughout the oxide layer. In one embodiment, for example, a first set of dual AC sputtering targets may include a 90/10 mixture of silicon and aluminum, and a second set of dual AC sputtering targets may include a 75/25 mixture of aluminum and silicon. In this embodiment, a first portion of the oxide layer can be deposited with the 90% Si/10% Al target, and a second portion can be deposited with the 75% Al/25% Si target. The resulting oxide layer has a gradient composition that changes from about 90% Si to about 25% Si (and conversely from about 10% Al to about 75% Al) through the thickness of the oxide layer.

In typical dual AC sputtering, homogeneous oxide layers are formed, and barrier performance from these homogeneous oxide layers suffer due to defects in the layer at the micro and nano-scale. One cause of these small scale defects is inherently due to the way the oxide grows into grain boundary structures, which then propagate through the thickness of the film.

Without wishing to be bound by any particular theory, it is currently believed that several effects contribute to the improved barrier properties of the gradient composition barriers described herein. One effect can be that greater densification of the mixed oxides occurs in the gradient region, and any paths that water vapor could take through the oxide are blocked by this densification. Another effect can be that by varying the composition of the oxide materials, grain boundary formation can be disrupted resulting in a microstructure of the film that also varies through the thickness of the oxide layer. Another effect can be that the concentration of one oxide gradually decreases as the other oxide concentration increases through the thickness, reducing the probability of forming small-scale defect sites. The reduction of defect sites can result in a coating having reduced transmission rates of water permeation.

In some exemplary embodiments, exemplary films can be subjected to post-treatments such as heat treatment, ultraviolet (UV) or vacuum UV (VUV) treatment, or plasma treatment. Heat treatment can be conducted by passing the film through an oven or directly heating the film in the coating apparatus, e.g., using infrared heaters or heating directly on a drum. Heat treatment may for example be performed at temperatures from about 30° C. to about 200° C., about 35° C. to about 150° C., or about 40° C. to about 70° C.

Other functional layers or coatings that can be added to the inorganic or hybrid film include an optional layer or layers to make the film more rigid. The uppermost layer of the film is optionally a suitable protective layer, such as optional inorganic layer 20. If desired, the protective layer can be applied using conventional coating methods such as roll coating (e.g., gravure roll coating) or spray coating (e.g., electrostatic spray coating), then cross-linked using, for example, UV radiation. The protective layer can also be formed by flash evaporation, vapor deposition and cross-linking of a monomer as described above. Volatilizable (meth)acrylate monomers are suitable for use in such a protective layer. In a specific embodiment, volatilizable (meth)acrylate monomers are employed.

Methods of Using Barrier Films

In a further aspect, the disclosure describes methods of using a barrier film made as described above in an article selected from a solid state lighting device, a display device, and combinations thereof. Exemplary solid state lighting devices include semiconductor light-emitting diodes (SLEDs, more commonly known as LEDs), organic light-emitting diodes (OLEDs), or polymer light-emitting diodes (PLEDs). Exemplary display devices include liquid crystal displays, OLED displays, and quantum dot displays.

Exemplary LEDs are described in U.S. Pat. No. 8,129,205. Exemplary OLEDs are described in U.S. Pat. Nos. 8,193,698 and 8,221,176. Exemplary PLEDs are described in U.S. Pat. No. 7,943,062.

Unexpected Results and Advantages

Exemplary barrier assemblies in articles or films of the present disclosure have a number of applications and advantages in the display, lighting, and electronic device markets as flexible replacements for glass encapsulating materials. Thus, certain exemplary embodiments of the present disclosure provide barrier assemblies in articles or films which exhibit improved moisture resistance when used in moisture barrier applications. In some exemplary embodiments, the barrier assemblies in articles or films can be deposited directly on a substrate that includes a moisture sensitive device, a process often referred to as direct encapsulation.

The moisture sensitive device can be, for example, an organic, inorganic, or hybrid organic/inorganic semiconductor device including, for example, a photovoltaic device such as a CIGS; a display device such as an OLED, electrochromic, or an electrophoretic display; an OLED or other electroluminescent solid state lighting device, or others. Flexible electronic devices can be encapsulated directly with the gradient composition oxide layer. For example, the devices can be attached to a flexible carrier substrate, and a mask can be deposited to protect electrical connections from the oxide layer deposition. A base (co)polymer layer and the oxide layer can be deposited as described above, and the mask can then be removed, exposing the electrical connections.

Exemplary embodiments of the disclosed methods can enable the formation of barrier assemblies in articles or films that exhibit superior mechanical properties such as elasticity and flexibility yet still have low oxygen or water vapor transmission rates. The barrier assemblies in articles or films have at least one inorganic or hybrid organic/oxide layer or can have additional inorganic or hybrid organic/oxide layers. In one embodiment, the disclosed barrier assemblies in articles or films can have inorganic or hybrid layers alternating with organic compound, e.g., (co)polymer layers. In another embodiment, the barrier assemblies in articles or films can includes an inorganic or hybrid material and an organic compound.

Barrier assemblies in articles or films formed using the disclosed method can have an oxygen transmission rate (OTR) less than about 1 cc/m$^2$-day, less than about 0.5 cc/m$^2$-day, or less than about 0.1 cc/m$^2$-day. Barrier assemblies in articles or films formed using the disclosed method can have an water vapor transmission rate (WVTR) less than about 10 cc/m$^2$-day, less than about 5 cc/m$^2$-day, or less than about 1 cc/m$^2$-day.

Exemplary embodiments of barrier assemblies in articles and barrier films according to the present disclosure are preferably transmissive to both visible and infrared light. The term "transmissive to visible and infrared light" as used herein can mean having an average transmission over the visible and infrared portion of the spectrum of at least about 75% (in some embodiments at least about 80, 85, 90, 92, 95, 97, or 98%) measured along the normal axis. In some embodiments, the visible and infrared light-transmissive assembly has an average transmission over a range of 400 nm to 1400 nm of at least about 75% (in some embodiments at least about 80, 85, 90, 92, 95, 97, or 98%). Visible and infrared light-transmissive assemblies are those that do not interfere with absorption of visible and infrared light, for example, by photovoltaic cells. In some embodiments, the visible and infrared light-transmissive assembly has an average transmission over a range wavelengths of light that are useful to a photovoltaic cell of at least about 75% (in some embodiments at least about 80, 85, 90, 92, 95, 97, or 98%). The first and second (co)polymeric film substrates, pressure sensitive adhesive layer, and barrier film can be selected based on refractive index and thickness to enhance transmission to visible and infrared light.

Exemplary embodiments of barrier assemblies in articles and barrier films according to the present disclosure are typically flexible. The term "flexible" as used herein with respect to a barrier film refers to being capable of being formed into a roll. In some barrier film embodiments, the term "flexible" refers to being capable of being bent around a roll core with a radius of curvature of up to 7.6 centimeters (cm) (3 inches), in some embodiments up to 6.4 cm (2.5 inches), 5 cm (2 inches), 3.8 cm (1.5 inch), or 2.5 cm (1 inch). In some embodiments, the flexible assembly can be bent around a radius of curvature of at least 0.635 cm (¼ inch), 1.3 cm (½ inch) or 1.9 cm (¾ inch).

Exemplary barrier assemblies in articles and barrier films according to the present disclosure generally do not exhibit delamination or curl that can arise from thermal stresses or shrinkage in a multilayer structure. Herein, curl is measured for barrier films using a curl gauge described in "Measurement of Web Curl" by Ronald P. Swanson presented in the 2006 AWEB conference proceedings (Association of Industrial Metallizers, Coaters and Laminators, Applied Web Handling Conference Proceedings, 2006). According to this method curl can be measured to the resolution of 0.25 m$^{-1}$ curvature. In some embodiments, barrier films according to the present disclosure exhibit curls of up to 7, 6, 5, 4, or 3 m$^{-1}$. From solid mechanics, the curvature of a beam is known to be proportional to the bending moment applied to it. The magnitude of bending stress is in turn is known to be proportional to the bending moment. From these relations the curl of a sample can be used to compare the residual stress in relative terms.

Barrier films also typically exhibit high peel adhesion to EVA, and other common encapsulants for photovoltaics, cured on a substrate. The properties of the barrier films disclosed herein typically are maintained even after high temperature and humidity aging.

Exemplary embodiments of the present disclosure have been described above and are further illustrated below by way of the following Examples, which are not to be construed in any way as imposing limitations upon the scope of the present disclosure. On the contrary, it is to be clearly understood that resort may be had to various other embodiments, modifications, and equivalents thereof which, after reading the description herein, may suggest themselves to those skilled in the art without departing from the spirit of the present disclosure and/or the scope of the appended claims.

EXAMPLES

The following examples are intended to illustrate exemplary embodiments within the scope of this disclosure. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. At the very least, and not as an attempt to limit the application of the doctrine of equivalents to the scope of the claims, each numerical parameter should at least be construed in light of the number of reported significant digits and by applying ordinary rounding techniques.

Materials

The following materials, abbreviations, and trade names are used in the Examples:

90% Si/10% Al targets were obtained from Materion Advanced Chemicals, Inc., Albuquerque, N. Mex.

ETFE film: Ethylene-tetrafluoroethylene film available from St. Gobain Performance Plastics, Wayne, N.J. under the trade name "NORTON® ETFE."

Solvents and other reagents used were obtained from Sigma-Aldrich Chemical Company (Milwaukee, Wis.), unless otherwise specified.

Table 1 lists the materials used to prepare (multi) (meth) acrylate (multi) silane compounds according to the foregoing disclosure:

Solvents and other reagents used were obtained from Sigma-Aldrich Chemical Company (Milwaukee, Wis.), unless otherwise specified.

Synthesis of Urethane (Multi)-(Meth)Acrylate (Multi)-Silane Precursor Compounds

Preparative Example 1

A 250 mL round bottom flask was charged with 8.79 g (0.086 mol) of propylene carbonate and 300 ppm of DBTDL in MEK solution and placed in a 55° C. oil bath. Using a pressure equalizing dropping funnel, 19.06 g (0.086 mol) of aminopropyltriethoxysilane (Dynasylan AMEO) was added over the course of 10 min. Heating was continued for 6 hours to provide a mixture of $(EtO)_3Si—(CH_2)_3—NH—C(O)—O—CH_2CH(CH_3)—OH$ and $(EtO)_3Si—(CH_2)_3—NH—C(O)—O—CH(CH_3)CH_2—OH$.

Preparative Example 2

A 250 mL three necked roundbottom flask equipped with an overhead stirrer was charged with 51.04 g (0.2063 mol, 247.37 MW) 3-triethoxysilylpropyl isocyanate. The flask was placed in a 55° C. oil bath, and after about 5 min, 882 microliters of a 10% solution of DBTDL in MEK (1000 ppm based on the total weight of reactants) was added to the reaction. Using a pressure equalizing dropping funnel, 23.96 g (0.2063mol, 116.12 MW) hydroxyethyl acrylate was added to the reaction over 2.5 hr. About one-half hour later, a Fourier Transform Infrared (FTIR) spectroscopic analysis was taken, showing disappearance of the isocyanate peak at 2265 cm$^{-1}$ to provide the product as an oil:

TABLE 1

Materials Used in the Examples

| Material Type | Trade Name or Acronym | Description |
|---|---|---|
| (Meth)Acrylate with hydroxyl-functionality | HEA | Hydroxyethyl acrylate available from Sigma Aldrich (Milwaukee, WI) |
| (Meth)Acrylate with hydroxyl-functionality | AHPM | 3-acryloxy-2-hydroxy-propyl methacrylate |
| (Meth)acrylated material with isocyanate functionality | IEA | Isocyanatoethyl acrylate available from CBC America Corp. (Commack, NY) |
| (Meth)acrylated material with isocyanate functionality | IEM | Isocyanatoethyl methacrylate available from CBC America Corp. (Commack, NY) |
| (meth)acrylated material w/ isocyanate functionality | BEI | 1,1-bis(acryloyloxymethyl) ethyl isocyanate available from CBC America Corp. (Commack, NY) |
| Catalyst | DBTDL | Dibutyltin dilaurate available from Sigma Aldrich (Milwaukee, WI) |
| Solvent | MEK | Methyl ethyl ketone available from EMD Chemicals, Inc. |
| Silane-functional and functional isocyanate | Geniosil GF 40 | 3-trimethoxysilylpropyl isocyanate available from Wacker Silicones (Adrian, MI) |
| Silane-functional and functional isocyanate | — | 3-triethoxysilylpropyl isocyanate available from Gelest, Inc. (Morrisville, PA) |
| Cyclic Azasilane | Cyclic AZA Silane 1932.4 | N-n-butyl-aza-2,2-dimethoxysilacylopentane available from Gelest, Inc. (Morrisville, PA) |

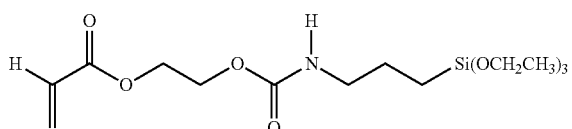

Preparative Example 3

In a manner similar to the preparation of Preparative Example 1, 49.15 g (0.1987 mol) 3-triethoxysilylpropyl isocyanate was reacted with 25.85 g (0.1987 mol, 130.14 MW) hydroxyethyl methacrylate in the presence of 882 microliters of a 10% solution of DBTDL in MEK (1000 ppm based on the total weight of reactants) to provide the product:

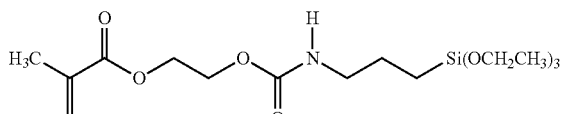

Preparative Example 4

In a fashion similar to the preparation of Preparative Example 1, 40.19 g (0.1625 mol) 3-triethoxysilylpropyl isocyanate was reacted with 34.81 g (0.1625 mol, 214.22 MW) 3-acryloxy-2-hydroxy-propyl methacrylate (AHPM) in the presence of 1000 ppm of DBTDL for about 24 hr, followed addition of 1.6 g (0.0075 mol) more AHPM and reaction for about 24 hr more to provide the product as an opaque white oil:

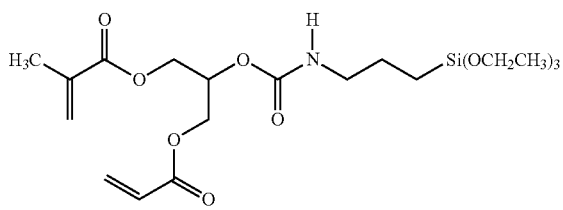

Preparative Example 5

In a fashion similar to the preparation of Preparative Example 1, 11.64 g (0.0894 mol) hydroxyethyl methacrylate was added to 18.36 g (0.0894 mol, 205.29 MW) 3-trimethoxysilylpropyl isocyanate and 176 microliters of 10% DBTDL in MEK (500 ppm) at 55° C. for 2 hr to provide the product:

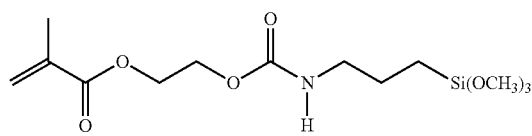

Preparative Example 6

In a fashion similar to the preparation of Preparative Example 1, 15.92 g (0.0715 mol, 214.22 MW) 3-acryloxy-2-hydroxy-propyl methacrylate (AHPM) was added to 14.68 g (0.0715 mol) 3-trimethoxysilylpropyl isocyanate in the presence of 500 ppm of DBTDL for about 5 h at 55° C. to provide the product:

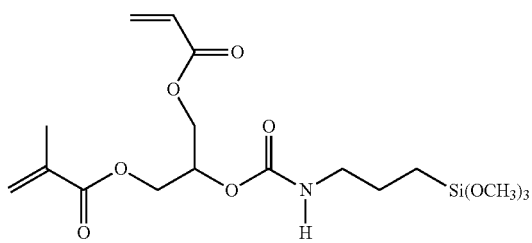

Preparative Example 7

A 500 mL roundbottom equipped with overhead stirrer was charged with 140.52 g (0.684 mol, 205 28 MW) 3-trimethoxysilylpropyl isocyanate and 0.22 g DBTDL and heated to 55° C. Using an addition funnel, 79.48 g (0.684 mol, 116.12 MW) hydroxyethyl acrylate was added over about 1 h. At about 4 h total, the product was isolated and bottled:

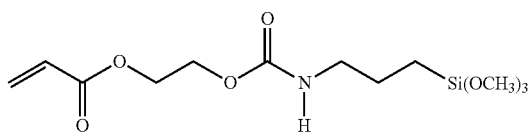

Composite Barrier Assembly and Barrier Film Preparation

Examples of multilayer composite barrier assemblies and barrier films were made on a vacuum coater similar to the coater described in U.S. Pat. No. 5,440,446 (Shaw et al.) and U.S. Pat. No. 7,018,713 (Padiyath, et al.).

Comparative Example 8 and Examples 9 through 11 below relate to forming simulated photovoltaice modules which were subjected to accelerated aging under conditions designed to simulate aging in an outdoor environment, and then subjected to a peel adhesion test to determine if the diurethane (meth)acrylate silanes of the above examples were effective in improving peel adhesion. Some procedures common to all these Examples are presented first.

Multilayer composite barrier films according to the examples below were laminated to a 0.05 mm thick ethylene tetrafluoroethylene (ETFE) film commercially available as NORTON® ETFE from St. Gobain Performance Plastics (Wayne, N.J.), using a 0.05 mm thick pressure sensitive adhesive (PSA) commercially available as 3M OPTICALLY CLEAR ADHESIVE 8172P from 3M Company (St. Paul, Minn.).

The laminated barrier sheets formed in each Example below was then placed atop a 0.14 mm thick polytetrafluoroethylene (PTFE) coated aluminum-foil commercially available commercially as 8656K61, from McMaster-Carr, Inc. (Santa Fe Springs, Calif.) with 13 mm wide desiccated edge tape commercially available as "SOLARGAIN Edge Tape SET LP01" from Truseal Technologies, Inc. (Solon, Ohio) placed around the perimeter of the foil between the barrier sheet and the PTFE.

A 0.38 mm thick encapsulant film commercially available as JURASOL from JuraFilms, Inc. (Downer Grove, Ill.) and an additional layer of the laminated barrier sheet were placed on the backside of the foil with the encapsulant between the barrier sheet and the foil. The multi-component constructions were vacuum laminated at 150° C. for 12 min.

Test Methods

Aging Test

Some of the laminated constructions described above were aged for 250 hours (hr) and 500 hours in an environmental chamber set to conditions of 85° C. and 85% relative humidity.

T-peel Adhesion Test

Unaged and aged barrier sheets were cut away from the PTFE surface and divided into 1.0 inch (25.4 mm) wide strips for adhesion testing using the ASTM D1876-08 T-peel test method. The samples were peeled by a peel tester commercially available as INISIGHT 2 SL equipped with TESTWORKS 4 software commercially available from MTS, Inc. (Eden Prairie, Minn.). A peel rate of 10 in/min (25.4 cm/min) was used. The reported adhesion value in Table II below is the average of four peel measurements.

Example 8 (Comparative)

This example is comparative in the sense that no coupling agents as described in Examples 1 through 7 were used. A polyetheylene terephthalate (PET) substrate film was covered with a stack of an acrylate smoothing layer, an inorganic silicon aluminum oxide (SiAlOx) barrier and an acrylate protective layer. The individual layers were formed as follows:

(Deposition of the (Meth)acrylate Smoothing Layer)

A 305 meter long roll of 0.127 mm thick by 366 mm wide PET film commercially available XST 6642 from Dupont of Wilmington, Del. was loaded into a roll-to-roll vacuum processing chamber. The chamber was pumped down to a pressure of $1 \times 10^{-5}$ Torr. The web speed was maintained at 4.8 meter/min while maintaining the backside of the film in contact with a coating drum chilled to −10° C. With the film in contact with the drum, the film surface was treated with a nitrogen plasma at 0.02 kW of plasma power. The film surface was then coated with tricyclodecane dimethanol diacrylate commercially available as SR-833S from Sartomer USA, LLC, Exton, Pa.).

More specifically, the diacrylate was degassed under vacuum to a pressure of 20 mTorr prior to coating, loaded into a syringe pump, and pumped at a flow rate of 1.33 mL/min through an ultrasonic atomizer operated at a frequency of 60 kHz into a heated vaporization chamber maintained at 260° C. The resulting monomer vapor stream condensed onto the film surface and was electron beam crosslinked using a multi-filament electron-beam cure gun operated at 7.0 kV and 4 mA to form a 720 nm (meth) acrylate layer.

(Deposition of the Inorganic Silicon Aluminum Oxide (SiAlOx) Barrier)

Immediately after the acrylate deposition and with the film still in contact with the drum, a SiAlOx layer was sputter-deposited atop the acrylate-coated web surface. Two alternating current (AC) power supplies were used to control two pairs of cathodes; with each cathode housing two 90% Si/10% Al targets commercially available from Materion of Albuquerque, N. Mex. During sputter deposition, the voltage signal from each power supply was used as an input for a proportional-integral-differential control loop to maintain a predetermined oxygen flow to each cathode. The AC power supplies sputtered the 90% Si/10% Al targets using 5000 watts of power, with a gas mixture containing 450 sccm argon and 63 sccm oxygen at a sputter pressure of 3.5 millitorr. This provided a 30 nm thick SiAlOx layer deposited atop the acrylate discussed above.

(Deposition of the (Meth)acrylate Protective Layer)

Immediately after the SiAlOx layer deposition and with the film still in contact with the drum, an acrylate protective layer second was coated and crosslinked on the same web generally using the same conditions as for the deposition of the smoothing layer, but with the following exceptions. The electron beam crosslinking was carried out using a multi-filament electron-beam cure gun operated at 7 kV and 5 mA. This provided a 720 nm thick acrylate layer atop Layer 2.

The resulting three layer stack on the polymeric substrate exhibited an average spectral transmission $T_{vis}$ of 87%, determined by averaging the percent transmission T between 400 nm and 700 nm, measured at a 0° angle of incidence. A water vapor transmission rate (WVTR) was measured in accordance with ASTM F-1249 at 50° C. and 100% relative humidity (RH) using MOCON PERMATRAN-W® Model 700 WVTR testing system commercially available from MOCON, Inc (Minneapolis, Minn.). The result was below the 0.005 g/m²/day lower detection limit rate of the apparatus.

The resulting three layer stack was used to form a simulated solar module construction as discussed in the section on general procedures above. These simulated solar modules were subjected to accelerated aging according to the aging test, and then the T-peel adhesion was assessed as discussed above. The results of the T-peel adhesion test are presented in Table 1 below.

Example 9

A polyethylene terephthalate (PET) substrate film was covered with a stack of an acrylate smoothing layer, an inorganic silicon aluminum oxide (SiAlOx) barrier and an acrylate protective layer containing the invention molecules. The individual layers were formed as in Comparative Example 8 except during the formation of the protective layer, instead of 100% tricyclodecane dimethanol diacrylate SR-833S being used, a mixture of 97% by weight of tricyclodecane dimethanol diacrylate SR-833S and 3% by weight of the compound synthesized in Preparatory Example 6 above was used instead.

The resulting three layer stack on the polymeric substrate exhibited an average spectral transmission $T_{vis}$=87% and a WVTR below the 0.005 g/m²/day, both tested as described in Comparative Example 8. Then the resulting three layer stack was used to form a simulated solar module construction as discussed in the section on general procedures above. These simulated solar modules were subjected to accelerated aging according to the aging test, and then the T-peel adhesion was assessed as discussed above. The results of the T-peel adhesion test are presented in Table 1 below.

Example 10

A polyethylene terephthalate (PET) substrate film was covered with a stack of an acrylate smoothing layer, an inorganic silicon aluminum oxide (SiAlOx) barrier and an acrylate protective layer containing the invention molecules. The individual layers were formed as in Comparative Example 8 except during the formation of the protective layer, instead of 100% tricyclodecane dimethanol diacrylate SR-833S being used, a mixture of 97% by weight of tricyclodecane dimethanol diacrylate SR-833S and 3% by weight of the compound synthesized in Preparatory Example 7 above was used instead.

The resulting three layer stack on the polymeric substrate exhibited an average spectral transmission $T_{vis}$=87% and a WVTR below the 0.005 g/m²/day, both tested as described in Comparative Example 8. Then the resulting three layer stack was used to form a simulated solar module construction as discussed in the section on general procedures above. These simulated solar modules were subjected to accelerated aging according to the aging test, and then the T-peel adhesion was assessed as discussed above. The results of the T-peel adhesion test are presented in Table 1 below.

Example 10 (Comparative)

A polyethylene terephthalate (PET) substrate film was covered with a stack of an acrylate smoothing layer, an inorganic silicon aluminum oxide (SiAlOx) barrier and an acrylate protective layer containing the disclosure molecules. The individual layers were formed as in Comparative Example 8 except during the formation of the protective layer, instead of 100% tricyclodecane dimethanol diacrylate SR-833S being used, a mixture of 97% by weight of tricyclodecane dimethanol diacrylate SR-833S and 3% by weight of N-n-butyl-AZA-2,2-dimethoxysilacyclopentane (commercially available from Gelest, Inc. (Morrisville, Pa.) under the product code 1932.4 was used instead.

The resulting three layer stack on the polymeric substrate exhibited an average spectral transmission $T_{vis}$=87% and a WVTR below the 0.005 g/m²/day, both tested as described in Comparative Example 8. Then the resulting three layer stack was used to form a simulated solar module construction as discussed in the section on general procedures above. These simulated solar modules were subjected to accelerated aging according to the aging test, and then the T-peel adhesion was assessed as discussed above. The results of the T-peel adhesion test are presented in Table 2 below.

TABLE 2

| Example | T-Peel Initial (N/cm) | T-Peel After 250 Hours Aging @ 85° C./85% RH (N/cm) | T-Peel After 1000 Hours Aging @ 85° C./85% RH (N/cm) |
|---|---|---|---|
| 7 (Comparative) | 0.3 | 0.1 | 0.1 |
| 8 | 10.4 | 10.4 | 11.2 |
| 9 | 3.6 | 10.9 | 11.0 |
| 10 (Comparative) | 6.0 | 10.1 | 0.4 |

While the specification has described in detail certain exemplary embodiments, it will be appreciated that those skilled in the art, upon attaining an understanding of the foregoing, may readily conceive of alterations to, variations of, and equivalents to these embodiments. Accordingly, it should be understood that this disclosure is not to be unduly limited to the illustrative embodiments set forth hereinabove. Furthermore, all publications, published patent applications and issued patents referenced herein are incorporated by reference in their entirety to the same extent as if each individual publication or patent was specifically and individually indicated to be incorporated by reference. Various exemplary embodiments have been described. These and other embodiments are within the scope of the following listing of disclosed embodiments and claims.

The invention claimed is:

1. An article, comprising:
   a substrate selected from a (co)polymeric film or an electronic device, the electronic device further comprising an organic light emitting device (OLED), an electrophoretic light emitting device, a liquid crystal display, a thin film transistor, a photovoltaic device, or a combination thereof;
   a base (co)polymer layer on a major surface of the substrate;
   an oxide layer on the base (co)polymer layer; and
   a protective (co)polymer layer on the oxide layer, wherein the protective (co)polymer layer comprises the reaction product of at least one urethane (multi)-(meth)acrylate (multi)-silane precursor compound of the formula:
   $R_S$—N(H)—C(O)—O—$R_A$ or $R_S$—O—C(O)—N(H)—$R_A$, wherein:
   $R_S$ is a silane containing group of the formula —$R^1$—[Si$(Y_p)(R^2)_{3-p}]_q$, further wherein:
   $R^1$ is a multivalent alkylene, arylene, alkarylene, or aralkylene group, said alkylene, arylene, alkarylene, or aralkylene groups optionally containing one or more catenary oxygen atoms,
   each Y is a hydrolysable group,
   $R^2$ is a monovalent alkyl or aryl group;
   p is 1, 2, or 3, and
   q is 1-5; and
   $R_A$ is a (meth)acryl group containing group of the formula $R^{11}$-(A)$_n$, wherein:
   $R^{11}$ is a polyvalent alkylene, arylene, alkarylene, or aralkylene group, said alkylene, arylene, alkarylene, or aralkylene groups optionally containing one or more catenary oxygen atoms,
   A is a (meth)acryl group comprising the formula $X^2$—C(O)—C($R^3$)=CH$_2$, further wherein:
   $X^2$ is —O, —S, or —NR$^3$,
   $R^3$ is H, or $C_1$-$C_4$, and
   n=1 to 5.

2. The article of claim 1, wherein Y is individually selected from the group consisting of alkoxy groups, acetate groups, aryloxy groups, and halogens.

3. The article of claim 1, wherein Y is selected from alkoxy groups.

4. The article of claim 1, further comprising a plurality of alternating layers of the oxide layer and the protective (co)polymer layer on the base (co)polymer layer.

5. The article of claim 1, wherein the substrate comprises a flexible transparent (co)polymeric film, optionally wherein the substrate comprises polyethylene terephthalate (PET), polyethylene napthalate (PEN), heat stabilized PET, heat stabilized PEN, polyoxymethylene, polyvinylnaphthalene, polyetheretherketone, fluoro(co)polymer, polycarbonate, polymethylmethacrylate, poly α-methyl styrene, polysulfone, polyphenylene oxide, polyetherimide, polyethersulfone, polyamideimide, polyimide, polyphthalamide, or combinations thereof.

6. The article of claim 1, wherein the base (co)polymer layer comprises a (meth)acrylate smoothing layer.

7. The article of claim 1, wherein the oxide layer comprises oxides and optionally any one or more of nitrides, carbides or borides of atomic elements from Groups IIA, IIIA, IVA, VA, VIA, VIIA, IB, or IIB, metals of Groups IIIB, IVB, or VB, rare-earth metals, or combinations thereof.

8. The article of claim 1, further comprising an oxide layer applied to the protective (co)polymer layer, optionally wherein the oxide layer comprises silicon aluminum oxide.

9. An electronic device incorporating the article according to claim 1, wherein the article is selected from a solid state lighting device, a display device, and combinations thereof.

10. A process, comprising:
(a) applying a base (co)polymer layer to a major surface of a substrate selected from a (co)polymeric film or an electronic device, the electronic device further comprising an organic light emitting device (OLED), an electrophoretic light emitting device, a liquid crystal display, a thin film transistor, a photovoltaic device, or a combination thereof;
(b) applying an oxide layer on the base (co)polymer layer; and
(c) depositing on the oxide layer a protective (co)polymer layer, wherein the protective (co)polymer layer comprises the reaction product of at least one urethane (multi)-(meth)acrylate (multi)-silane precursor compound of the formula:
$R_S$—N(H)—C(O)—O—$R_A$ or $R_S$—O—C(O)—N(H)—$R_A$, wherein:
$R_S$ is a silane containing group of the formula —$R^1$—[Si$(Y_p)(R^2)_{3-p}]_q$, further wherein:
$R^1$ is a multivalent alkylene, arylene, alkarylene, or aralkylene group, said alkylene, arylene, alkarylene, or aralkylene groups optionally containing one or more catenary oxygen atoms,
each Y is a hydrolysable group,
$R^2$ is a monovalent alkyl or aryl group;
p is 1, 2, or 3, and
q is 1-5; and
$R_A$ is a (meth)acryl group containing group of the formula $R^{11}$-$(A)_n$, wherein:
$R^{11}$ is a polyvalent alkylene, arylene, alkarylene, or aralkylene group, said alkylene, arylene, alkarylene, or aralkylene groups optionally containing one or more catenary oxygen atoms,
A is a (meth)acryl group comprising the formula $X^2$—C(O)—C($R^3$)=$CH_2$, further wherein:
$X^2$ is —O, —S, or —$NR^3$,
$R^3$ is H, or $C_1$-$C_4$, and
n=1 to 5.

11. The process of claim 10, wherein Y is selected from the group consisting of alkoxy groups, acetate groups, aryloxy groups, and halogens.

12. The process of claim 10, wherein the at least one urethane (multi)-(meth)acrylate (multi)-silane precursor compound precursor compound undergoes a chemical reaction to form the protective (co)polymer layer at least in part on the oxide layer, optionally wherein the chemical reaction is selected from a free radical polymerization reaction, and a hydrolysis reaction.

13. The process of claim 10, wherein step (a) comprises:
(i) evaporating the base (co)polymer precursor;
(ii) condensing the evaporated base (co)polymer precursor onto the substrate; and
(iii) curing the evaporated base (co)polymer precursor to form the base (co)polymer layer.

14. The process of claim 10, wherein the base (co)polymer precursor comprises a (meth)acrylate monomer.

15. The process of claim 10, wherein step (b) comprises depositing an oxide onto the base (co)polymer layer to form the oxide layer, wherein depositing is achieved using sputter deposition, reactive sputtering, chemical vapor deposition, or a combination thereof.

16. The process of claim 10, wherein step (b) comprises applying a layer of an inorganic silicon aluminum oxide to the base (co)polymer layer.

17. The process of claim 10, further comprising sequentially repeating steps (b) and (c) to form a plurality of alternating layers of the protective (co)polymer layer and the oxide layer on the base (co)polymer layer.

18. The process of claim 10, wherein step (c) further comprises at least one of co-evaporating the at least one urethane (multi)-(meth)acrylate (multi)-silane precursor compound precursor compound with a (meth)acrylate compound from a liquid mixture, or sequentially evaporating the at least one urethane (multi)-(meth)acrylate (multi)-silane precursor compound precursor compound and a (meth)acrylate compound from separate liquid sources, optionally wherein the liquid mixture comprises no more than about 10 wt. % of the urethane (multi)-(meth)acrylate (multi)-silane precursor compound precursor compound.

19. The process of claim 10, wherein step (c) further comprises at least one of co-condensing the urethane (multi)-(meth)acrylate (multi)-silane precursor compound precursor compound with the (meth)acrylate compound onto the oxide layer, or sequentially condensing the urethane (multi)-(meth)acrylate (multi)-silane precursor compound precursor compound and the (meth)acrylate compound on the oxide layer.

20. The process of claim 10, wherein reacting the urethane (multi)-(meth)acrylate (multi)-silane precursor compound precursor compound with the (meth)acrylate compound to form a protective (co)polymer layer on the oxide layer occurs at least in part on the oxide layer.

* * * * *

UNITED STATES PATENT AND TRADEMARK OFFICE
CERTIFICATE OF CORRECTION

PATENT NO. : 9,790,396 B2
APPLICATION NO. : 14/416303
DATED : October 17, 2017
INVENTOR(S) : Thomas Klun It is certified that error appears in the above-identified patent and that said Letters Patent is hereby corrected as shown below:

On the Title Page

Column 2 (Abstract)
Line 9, Delete "(multi) (meth)acrylate" and insert -- (multi)-(meth)acrylate --, therefor.

Page 3, Column 2 (Other Publications)
Lines 23-24, Delete "urehtane/urea" and insert -- urethane/urea --, therefor.

In the Specification

Column 2
Line 52, Delete "napthalate" and insert -- naphthalate --, therefor.

Column 6
Line 1, Delete "itself" and insert -- itself. --, therefor.

Column 9
Line 36, Delete "pentaetrythritol" and insert -- pentaerythritol --, therefor.

Column 10
Line 33, Delete "napthalate" and insert -- naphthalate --, therefor.

Column 13
Line 25, Delete "HA," and insert -- IIA, --, therefor.

Column 24
Line 46, Delete "photovoltaice" and insert -- photovoltaic --, therefor.

Signed and Sealed this
Twenty-second Day of May, 2018

Andrei Iancu
*Director of the United States Patent and Trademark Office*

Column 25
Line 21, Delete "INISIGHT" and insert -- INSIGHT --, therefor.
Line 31, Delete "polyetheylene" and insert -- polyethylene --, therefor.

In the Claims

Column 28
Line 54, In Claim 5, delete "napthalate" and insert -- naphthalate --, therefor.

Column 29
Lines 49-50, In Claim 12, after "(multi)-silane" delete "precursor compound".

Column 30
Lines 28-29 (Approx.), In Claim 18, after "(multi)-silane" delete "precursor compound".
Line 32 (Approx.), In Claim 18, after "(multi)-silane" delete "precursor compound".
Line 36 (Approx.), In Claim 18, after "(multi)-silane" delete "precursor compound".
Line 39 (Approx.), In Claim 19, after "(multi)-silane" delete "precursor compound".
Line 42 (Approx.), In Claim 19, after "(multi)-silane" delete "precursor compound".
Line 46 (Approx.), In Claim 20, after "(multi)-silane" delete "precursor compound".

UNITED STATES PATENT AND TRADEMARK OFFICE
CERTIFICATE OF CORRECTION

| | | |
|---|---|---|
| PATENT NO. | : 9,790,396 B2 | Page 1 of 1 |
| APPLICATION NO. | : 14/416303 | |
| DATED | : October 17, 2017 | |
| INVENTOR(S) | : Thomas P Klun | |

It is certified that error appears in the above-identified patent and that said Letters Patent is hereby corrected as shown below:

In the Specification

Column 1
Line 14, insert:
--GOVERNMENT RIGHTS
This invention was made with Government support under DE-EE0004739 awarded by DOE. The Government has certain rights in this invention.--

Signed and Sealed this
Twenty-second Day of October, 2024

Katherine Kelly Vidal
*Director of the United States Patent and Trademark Office*